United States Patent
Wu et al.

(10) Patent No.: US 6,525,242 B1
(45) Date of Patent: Feb. 25, 2003

(54) PROPAGATION OF HUMAN HEPATOCYTES IN NON-HUMAN MAMMALS

(75) Inventors: George Y. Wu, Avon, CT (US); Catherine H Wu, Avon, CT (US)

(73) Assignee: The University of Connecticut, Farmington, CT (US)

(*) Notice: Subject to any disclaimer, the term of this patent is extended or adjusted under 35 U.S.C. 154(b) by 0 days.

(21) Appl. No.: 09/431,901

(22) Filed: Nov. 2, 1999

(51) Int. Cl.$^7$ .................... A01K 67/00; A01K 67/033; A01K 67/027

(52) U.S. Cl. .................... 800/8; 800/3; 800/9; 800/13; 800/18

(58) Field of Search .................... 424/93.1, 93.2, 424/189.1, 422, 423; 435/325, 370, 6, 375; 536/24.5; 800/3, 8, 21, 9, 13, 18

(56) References Cited

U.S. PATENT DOCUMENTS

| | | | |
|---|---|---|---|
| 5,759,830 A | 6/1998 | Vacanti et al. | 435/180 |
| 5,858,328 A | 1/1999 | Reisner | 424/9.2 |
| 6,034,297 A | 3/2000 | Vierling | 800/9 |

FOREIGN PATENT DOCUMENTS

| | | |
|---|---|---|
| WO | 9318144 | 9/1993 |
| WO | 9402601 | 3/1994 |
| WO | 9427556 | 12/1994 |
| WO | 9509235 | 4/1995 |
| WO | 9639810 | 12/1996 |
| WO | 0017338 | 3/2000 |
| WO | 0118193 | 3/2001 |

OTHER PUBLICATIONS

Pages et al. Human Gene Therapy. 6: 21–30, Jan. 1995.*
Soriano et al. Transplantation Proceedings. 24(6): 3020–3021, Dec. 1992.*
Sacci et al. Proc. Natl. Acad. Sci. USA. 89: 3701–3705, May 1992.*
Main et al, "Hepatitis", Chap. 51, Antibiotic Chemotherapy, 7th ed., pp. 721–731, 1997.*
Dorling et al, Lancet. 349: 867–871, Mar. 1997.*
Verma et al. Nature. 389: 239–242, Sep. 1997.*
Gordon et al. Diabetes. 47 (8): 1199–1206, Jan. 1995.*
Mullins et al., Perspective Series: Molecular Medicine in Generically Engineered Animals, Journal of Clinical Investigation, 1996, vol. 98, No. 11, pp. 537–539.*
Kline et al., Development of tolerance to experimental cardiac allografts in untero, Ann Thorac Surg, Jan. 1994, National Library of Medicine, 1 page.*
Brown et al., 2000, "A long–term hepatitis B viremia model generated by transplanting nontumorigenic immortalized human hepatocytes in Rag–2–deficient mice", Hepatology 31:173–181.

Ohashi et al., 2000, "Sustained survival of human hepatocytes in mice: a model for in vivo infection with human hepatitis delta viruses", Nat. Med. 6:327–331.
Cohen, 1999, "The scientific challenge of hepatitis C", Science 285:26–30.
Dienstag et al, 1999, "Lamivudine al initial treatment for chronic hepatitis B in the United States", New Eng. J. Med. 341:1256–1263.
Friend et al., 1999, "Engineering hepatocyte spheroids for potential application in a bioartificial liver", http://www.cems.umn.edu/~wshu_grp/bal/balold.html.
Ilan et al., 1999, "The hepatitis B virus–trimera mouse: a model for human HBV infection and evaluation of anti –HBV therapeutic agents", Hepatology 29:553–562.
Jung et al., 1999, "Initiation of mammalian liver development from endoderm by fibroblast growth factors", Science 284:1998–2002.
Lohmann et al., 1999, "Replication of subgenomic hepatitis C virus RNAs in a hepatima cell line", Science 285:110–113.
Mooney and Mikos, 1999, "Growing new organs", Scientif. Am. http://www.sciam.com:80/1999/0499issue/0499mooney.html.
Ouyang et al., 1999, "A approach for obtaining functional human hepatocytes in livers of immunocompetent rats", Hepatology 30:252A.
Taylor et al., 1999, "Inhibition of interferon–inducible protein kinase PKR by HCV E2 protein", Science 285:107–110.
Thomas, 1999, "Hepatitis C virus dynamics in vivo and the antiviral efficacy of interferon alfa therapy", Hepatology 29:1333–1334.
Bumgardner et al., 1998, "A functional model of hepatocyte transplantation for in vivo immunologic studies", Transplantation 65:53–61.
*Clonetics 1998–1999: Normal Human Cell Systems Catalog*, 1998.
Davis et al., 1998, "Interferon alpha–2b alone or in combination with ribavirin for the treatment of relapse of chronic hepatitis C", N. Eng. J. Med. 339:1493–1499.
Gordon et al., 1998, "Prolonged survival of rat islet and skin xenografts in mice treated with donor splenocytes and anti–CD154 monoclonal antibody", Diabetes 47:1199–1206.

(List continued on next page.)

*Primary Examiner*—Anne-Marie Baker

(57) ABSTRACT

The present invention relates to the preparation of non-human animals having chimeric livers, whereby some or substantially all of the hepatocytes present are human hepatocytes. It is based, at least in part, on the discovery that rats, tolerized in utero against human hepatocytes, were found to serve as long-term hosts for human hepatocytes introduced post-natally, and the introduced hepatocytes maintained their differentiated phenotype, as evidenced by continued production of human albumin.

9 Claims, 14 Drawing Sheets

Figure 1:
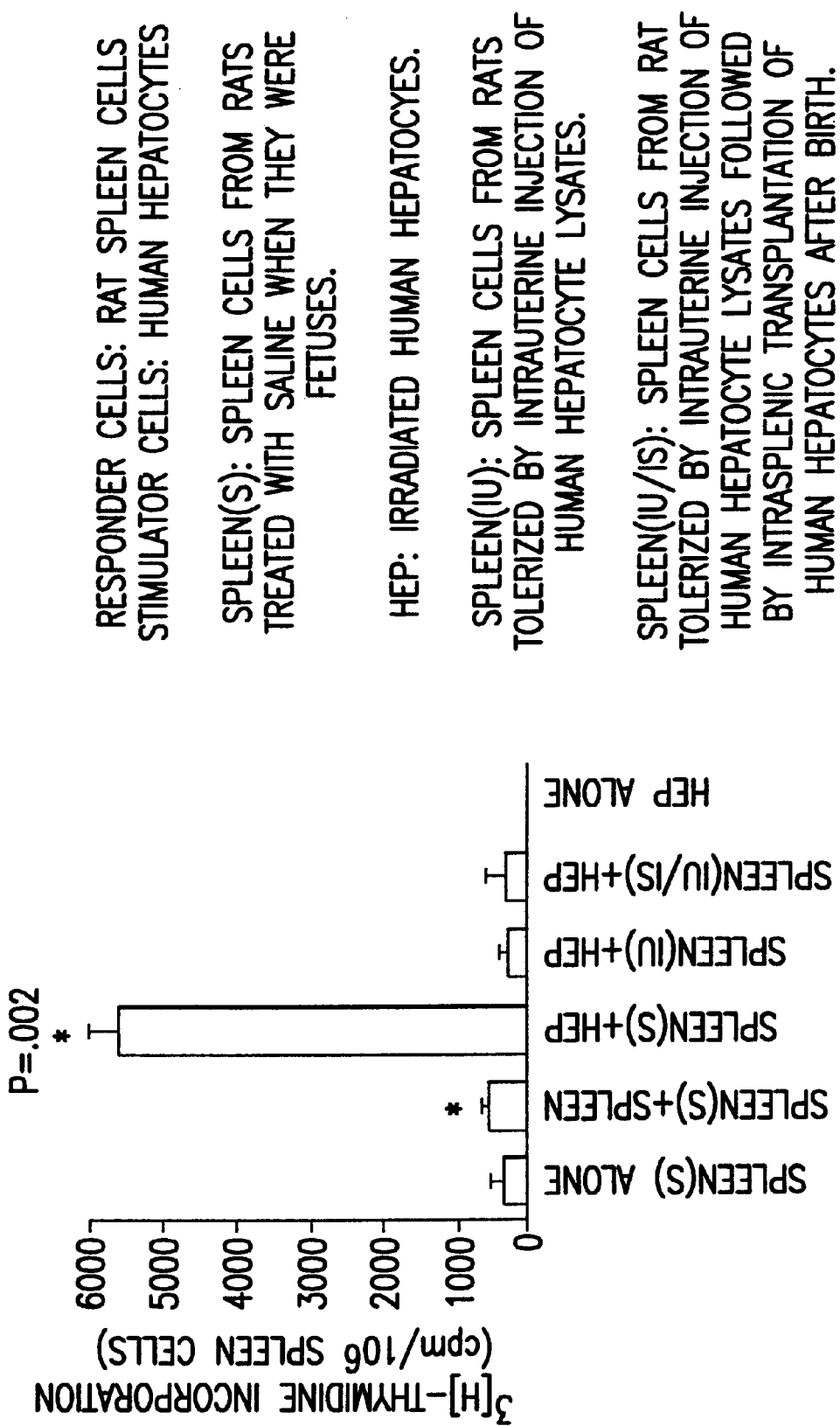

(7 of 14 Drawing Sheet(s) Filed in Color)

OTHER PUBLICATIONS

Liang, 1998, "Combination therapy for hepatitis C infection", N. Eng. J. Med. 339:1549–1550.

McHutchison et al., 1998, "Interferon alpha–2b alone or in combination with ribavirin as initial treatment for chronic hepatitis C", N. Eng. J. Med. 339:1485–1492.

Peterson et al., 1998, "Liver repopulation with xenogenic hepatocytes in B and T cell–deficient mice leads to chronic hepadnavirus infection and clonal growth of hepatocellular carcinoma", Proc. Natl. Acad. Sci. U.S.A., 95:310–315.

Poynard et al., 1998, "Randomised trial of interferon α2b plus ribavarin for 48 weeks or 24 weeks versus interferon α2b plus placebo for 48 weeks for treatment of chronic infection with hepatitis C virus", Lancet 352:1426–1432.

Attavar et al., 1997, "Mechanisms of intrathymic tolerance induction to isolated rat hepatocyte allografts", Hepatology 26:1287–1295.

Clarke, 1997, "Molecular virology of hepatitis C virus", J. Gen. Virol., 78:2397–2410.

Cusick et al., 1997, "The effect of donor and recipient age on engraftment of tissue engineered liver", J. Ped. Surg. 32:357–360.

*Introductory Immunobiology,* 1997 Davies ed., Chapman and Hall, London, p. 366.

Kolykhalov et al., 1997, "Transmission of hepatitis C by intrahepatic inoculation with transcribed RNA", Science 277:570–574.

Major and Feinstone, 1997, "The molecular virology of hepatitis C", Hepatology 25:1527–1538.

Markus et al., 1997, "Selective intraportal transplantation of DiI–marked isolated rat hepatocytes", Cell Transplantation 6:455–462.

Marucci et al., 1997, "Effect of xanthine analog on human hepatocellular carcinome cells (Alexander) in culture and in xenografts in SCID mice", Hepatology 26:1195–1202.

Santoro and Joyce, 1997, "A general purpose RNA–cleaving DNA enzyme", Proc. Natl. Acd. Sci. U.S.A. 94:4262–4266.

Sugiyama et al., 1997, "Genetic analysis of the hepatitis C virus (HCV) genome from HCV–infected human T cells", J. Gen. virol. 78:329–336.

Yuh et al., 1997, "A rodent model of in utero chimeric tolerance induction", J. Heart Lung Transpl. 16:222–230.

Ganem, 1996, "Hepadnaviridae and their replication", In Fields et al eds., *Fields Virology,* Lippincott–Raven, Philidelphia, PA, pp. 2703–2737.

Gupta et al., 1996, "Hepatocyte transplantation: progress toward liver repopulation", Prog. Liv. Dis. 14:199–222.

Hadju et al., 1996, "In vitro allogenic hematopoietic stem cell transplantation to induce tolerance", Fetal Diagnosis and Therapy 11:241–248.

Hollinger, 1996, "Hepatitis B Virus" *Fields Virology,* 1996, Third Edition, Fields et al. eds, Lippincott–Raven, New York, pp. 2739–2742, 2748–2751.

Ito et al., 1996, "Cultivation of hepatitis C virus in primary hepatocyte culture from patients with chronic hepatitis C results in release of high titre infectious virus", J. Gen. Virol. 77:1043–1054.

Jauregui et al., 1996, "Use of mammalian liver cells for artificial liver support", Cell Transplantation 5:353–367.

Lieber et al., 1996, "elimination of hepatitis C virus RNA in infected human hepatocytes by adenovirus–mediated expression of ribozymes", J. Virol. 70:8782–8791.

Nakajima et al., 1996, "Characterization of long–term cultures of hepatitis C virus", J. Virol. 70:3325–3329.

Su et al., 1996, "Selective killing of AFP–positive hepatocellular carcinoma cells by adeno–associated virus transfer of the herpes simplex virus thymidine kinase gene", Human Gene Therapy, 7:463–470.

Cribier et al., 1995, "In vitro infection of peripherial blood mononuclear cells by hepatitis C virus", J. Gen. Virol. 76:2485–2491.

Fabrega et al., 1995, "Amelioration of analbuminemia by transplantation of allogenic hepatocytes in tolerized rats", Transplantation 59:1362–1364.

Galun et al., 1995, "Hepatitis C virus viremia in SCID→BNX mouse chimera", J. Infect. Dis. 172:25–30.

Kato et al., 1995, "Susceptibility of human T–lymphocytropic virus type I infected cell line MT–2 to hepatitis C virus infection", Biochem. Biophys. Res. Commun. 206:863–869.

Lanford et al., 1995, "Lack of detection of negative–strand hepatitis C virus RNA in peripheral blood mononuclear cells and other extrahepatic tissues by the highly strand–specific rTth reverse transcriptase PCR", J. Virol. 69:8079–8083.

Lieber et al., 1995, "Adenovirus–mediated urokinase gene transfer induces liver regeneration and allows for efficient retrovirus transduction of hepatocytes in vivo", Proc. Natl. Acad. Sci. U.S.A., 92:6210–6214.

Mitzutani et al., 1995, "Inhibition of hepatitis C virus replication by antisense oligonucleotide in culture cells", Biochem. Biophys. Res. Commun. 212:906–911.

Onodera et al., 1995, "Long–term effect of intrasplenic hepatocyte transplantation in cogenitally ascorbic acid biosynthetic enzyme–deficient rats", Cell Transpl. 4:S41–S43.

Rhim et al., 1995, "Complete reconstitution of mouse liver with xenogenic hepatocytes", Proc. Natl. Acad. Sci. U.S.A. 92:4942–4946.

Rozga et al., 1995, "Repeated intraportal hepatocyte transplantation in analbuminemic rats", Cell Transpl. 4:237–243.

Salomon et al., 1995, "A truncated herpes simplex virus thymidine kinase phosphorylates thymidine and nucleoside analogs and does not cause sterility in transgenic mice", Mol. Cell. Biol. 15:5322–5328.

Smythe et al., 1995, "Treatment of experimental human mesothelioma using adenovirus transfer of the herpes simplex thymidine kinase gene", Ann. Surg. 222:78–86.

Yoo et al., 1995, "Transfection of a differentiated human hepatoma cell line (Huh 7) with in vitro–transcribed hepatitis C virus (HCV) RNA and establishment of a long–term culture persistently infected with HCV", J. Gen. Virol. 69:32–38.

Grossman et al., 1994, "Successful ex vivo gene therapy directed to liver in a patient with familial hypercholesterolaemia", Nat. Genet. 6:335–341.

Heard, 1994, "Current theraputic relevance of liver gene transfer", Hepatology 20:253–256.

Kline et al., 1994, "Development of tolerance to experimental cardiac allografts in utero", Ann. Thorac. Surg. 57:72–75.

Kolberg et al., 1994, "The bystander effect in gene therapy: great, but how does it work?", J. NIH Res. 6:62–64.

Lanford et al., 1994, "Demonstration of in vitro infection of chimpanzee hepatocytes with hepatitis C virus using strand specific RT/PCR", Virol. 202:606–614.

Rhim et al., 1994, "Replacement of diseased mouse liver by hepatic cell transplantation", Science 263:1149–1152.

Rivas et al., 1994, "Transplantation of hepatocytes: an in–vitro and in–vivo study in canines", Cell Tranplantation 3:193–201.

Shimizu and Yoshikura, 1994, "Multicycle infection of hepatitis C virus in cell culture and inhibition by alpha and beta interferons", 68:8406–8408.

Willems et al., 1994, "Hepatitis virus C–RNAs in plasma and in peripherial blood mononuclear cells of hemophiliacs with chronic hepatitis C", J. Med. Virol. 42:272–278.

Bertolini et al., 1993, "The human bone–marrow–derived B–cell line CE, susceptible to hepatitis C virus infection", Res. Virol. 144:281–285.

Holzman et al., 1993, "Selective intraportal hepatocyte transplantation in analbuminemic and Gunn rats", Transplantation 55:1213–1219.

Iacovacci et al., 1993, "Replication and multiplication of hepatitis C virus genome in human foetal liver cells", Res. Virol. 144:275–279.

Mito et al., 1993, "Hepatocyte transplantation for hepatic failure", Transplant Rev. 7:35–43.

Takeshita et al., 1993, "Hepatocellular transplantation for metabolic support in experimental acute ischemic liver failure in rats", Cell Transplantation 2:319–324.

Culver et al., 1992, "In vivo gene transfer with retroviral vector–producer cells for treatment of experimental brain tumors", Science 256:1550–1552.

Sanhadji et al., 1992, "Transplantation in various murine models", Bone Marrow Transplantation 9:77–82.

Shimizu et al., 1992, "Evidence for in vitro replication of hepatitis C virus genome in a human T–cell line", Proc. Natl. Acad. Sci. U.S.A., 89:5477–5481.

Vemura et al., 1992, "Immune tolerance to a defined heterologous antigen after intrasplenic hepatocyte transplantation: implications for gene therapy", FASEB 6:2836–2842.

Wilson et al., 1992, "Hepatocyte–directed gene transfer in vivo leads to transient improvement of hypercholesterolemia in low density lipoprotein receptor–deficient rabbits", J. Biol. Chem. 267:963–967.

Yuh et al., 1992, "Transcriptional regulation of precore and pregenomic RNAs of hepatitis B virus" J. Virol. 66:4073–4084.

Zignego et al., 1992, "Infection of peripheral mononuclear blood cells by hepatitis C virus", J. Hepatology 15:382–386.

Blum et al., 1991, "Naturally occurring misense mutation in the polymerase gene terminating hepatitis B virus replication", J. Virol. 65:1836–1842.

Choo et al., 1991, "Genetic organization and diversity of the hepatitis C virus", Proc. Natl. Acad. Sci. U.S.A., 88:2451–2455.

Okamoto et al., 1991, "nucleotide sequence of the genomic RNA of hepatitis C virus isolated from a human carrier: comparison with reported isolates for conserved and divergent regions", J. Gen. Virol. 72:2697–2704.

Ponder et al., 1991, "Mouse hepatocytes migrate to liver parenchyma and function indefinitely after intrasplenic transplantation", Proc. Natl. Acad. Sci. U.S.A. 88:1217–1221.

Sandgren et al., 1991, "Complete hepatic regeneration after somatic deletion of an albumin–plasminogen activator transgene", Cell 66:245–256.

Streilein, 1991, "Neonatal tolerance of H–2 alloantigens: procuring graft acceptance the 'old–fashioned' way", Transplantation 52:1–10.

Takamizawa et al., 1991, "Structure and organization of the hepatitis C virus genome isolated from human carriers", J. Virol. 65:1105–1113.

Touraine, 1991, "In utero transplantation of fetal liver stem cells in humans", Blood cells 17:379–387.

Wilson et al., 1991, "Transplantation of allogenic hepatocytes into LDL receptor deficient rabbits leads to transient improvement in hypercholesterolemia", Clin. Biotechnol. 3:21–26.

Wu et al., 1991, "Receptor–mediated gene delivery in vivo: partial correction of genetic analbuminemia in nasage rats", J. Biol. Chem. 266:14338–14342.

Heckel et al., 1990, "Neonatal bleeding in transgenic mice expressing urokinase–type plasminogen activator" Cell 62:447–456.

Kato et al., 1990, "Molecular cloning of the human hepatitis C virus genome from Japanese patients with a non–A, non–B hepatitis", Proc. Natl. Acad. Sci. U.S.A., 87:9524–9528.

Powell and Streilein, 1990, "Neonatal tolerance induction by class II alloantigens activates IL–4–secreting, tolerogen–responsive T cells", J. Immunol. 144:854–859.

Wiederkehr et al., 1990, "Hepatocyte transplantation for the low–density lipoprotein receptor–deficient state" Transplant. 50:466–476.

Berchtold, 1989, "A simple method for direct cloning and sequencing cDNA by the use of a single specific oligonucleotide and oligo(dT) in a polymerase chain reaction (PCR)", Nuc. Acids Res.17:453.

Carlson et al., 1989, "Accumulation of PiZ $\alpha_1$–antitrypsin causes liver damage in transgenic mice", J. Clin. Invest. 83:1183–1190.

Chang et al., 1989, "Biosynthesis of the reverse transcriptase of hepatitis B viruses involves de novo translational initiation not ribosomal frameshifting", Nature 337:364–368.

Choo et al., 1989, "Isolation of a cDNA clone derived from a blood–borne non–A, non–B viral hepatitis genome", Science 244:359–362.

Moscioni et al., 1989, "Human liver cell transplantation: prolonged function in athymic–Gunn and athymic–analbuminemic hybrid rats", Gastroenterol. 96:15461551.

Ramsdell et al., 1989, "A nondeletional mechanism of thymic self tolerance", Science 246:1038–1041.

Zucker, 1989, "On finding all suboptimal foldings of an RNA molecule", Science 244:48–52.

Demetriou et al., 1988, "Transplantation of microcarrier–attached hepatocytes into 90% partially hepatectomized rats", Hepatology 8:1006–1009.

Maganto et al, 1988, "Effect of Ciclosporin on allogenic hepatocyte transplantation: a morphological study", Eur. Surg. Res. 20:248–253.

McDuffie et al., 1988, Involvement of major histocompatibility complex products in tolerance induction in the thymus, J. Immunol. 141:1840–1847.

Pullen et al., 1988, "The T–cell repertoire is heavily influenced by tolerance to polymorphic self–antigens", Nature 335:796–801.

Sells et al., 1988, "Replicative intermediates of hepatitis B virus in HepG2 cells that produce infectious virions", J. Virol. 62:2836–2844.

Chomczynski and Sacchi, 1987, "Single–step method of RNA isolation by acid guanidinium thiocyanate–phenol–chloroform extraction", Anal. Biochem. 162:156–159.

Cobourn et al., 1987, "Allogenic intrasplenic hepatocyte transplantation in the Gunn rat using cyclosporine A immunosuppression", Transpl. Proc. 19:1002–1003.

Farber and Sarma, 1987, "Chemical carcinogenesis: the liver as a model", in *Concepts and Theories in Carcinogenesis,* Maskens et al., eds, Elsevier, Amsterdam, pp. 185–220.

Kappler et al., 1987, T cell tolerance by clonal elimination in the thymus, Cell 49:273–280.

Will et al., 1987, "Replication strategy of human hepatitis B virus", J. Virol. 61:904–911.

Darby et al., 1986, "Observations on rat spleen reticulum during the development of syngeneic hepatocellular implants", Br. J. Exp. Pathol. 67:329–339.

Makowka et al., 1986, "Allogenic hepatocyte transplantation in the rat spleen under cyclosporine immunosuppression", Transplantation 42:537–541.

Seeger et al., 1986, Biochemical and genetic evidence for the hepatitis B virus replication strategy, Science 232:477–484.

Krumlauf et al., 1985, "Regulated expression of $\alpha$–fetoprotein genes in transgenic mice", Cold Spring Harbor Symp. Quant. Biol. 5–0:371–378.

De Clercq, 1984, "Biochemical aspects of the selective antiherpes activity of nucleoside analogues", Biochem. Biopharmacol. 33:2159–2169.

Gerber et al., 1983, "Phenotypic characterization of hepatic proliferation: antigenic expression by proliferating epithelial cells in fetal liver, massive hepatic necrosis and nodular transformation of the liver", AJP 110:70–74.

Guguen–Guillouzo et al., 1982, "High yield preparation of isolated human adult hepatocytes by enzymatic perfusion of the liver", Cell. Biol. Int. Rep. 6:625–628.

Osborn and Webber, 1982, "Immunofluoresence and immunocytochemical procedures with affinity purified antibodies: tubulin–containing structures", Meth. Cell. Biol. 24:97–132.

Palmiter et al., 1982, "Differential regulation of metallithionein–thymidine kinase fusion genes in transgenic mice and their offspring", Cell 29:701–710.

Summers and Mason, 1982, Replication of the genome of a hepatitis B–like virus by reverse transcription of an RNA intermediate, Cell 29:403–415.

Feinstone et al., 1981, "Non–A, non–B hepatitis in chimpanzees and marmosets", J. Infect. Dis. 144:588–598.

Knodell et al., 1981, "The woeful cation: mechanisms for its hepatic uptake", Hepatology 1:524.

Bradley, 1980, "Mixed Lymphocytes Responses", in *Selected Methods in Cellular Immunology,* Mishell and Shiigi eds., WH Freeman and Co., p. 162–172.

Henry and Watson, 1980, "Immunization in microsuspension cultures", in *Selected Methods in Cellular Immunology,* Mishell and Shiigi eds., WH Freeman and Co., p. 65–68.

Sommer et al., 1979, "Hepatocellular transplantation for treatment of D–galactosamine–induced acute liver failure in rats", Transplant Proc. 11:578–584.

Fyfe et al., 1978, "Thymidine kinase from herpes simplex virus phosphorylates the new antiviral compound, 9–(2–hydroxyethoxymethyl)guanine", J. Biol. Chem. 253:8721–8727.

Groth et al., 1977, "Correction of hyperbilirubinemia in the glucuronyltransferase–deficient rat by intraportal hepatocyte transplantation", Transpl. Proc. 9:313–316.

Sutherland et al., 1977, "Hepatic transplantation in acute liver failure", Surgery 82:124–132.

Matas et al., 1976, "hepatocellular transplantation for metabolic deficiencies:decrease of plasma bilirubin in Gunn rats", Science 192:892–894.

Seglen et al., 1976, "Preparation of rat liver cells", Methods Cell Biol. 13:29.

Aviv and Leder, 1972, "Purification of biologically active globin messenger RNA by chromatography on oligothymidic acid–cellulose", Proc. Natl. Acad. Sci. U.S.A., 69:1408–1412.

Scheffe, 1959, *The analysis of variance,* John Wiley and Sons, New York, NY, p. 247.

Billingham et al., 1953, Actively acquired tolerance of foreign cells, Nature 172:603–606.

* cited by examiner

1: 10 ng standard human albumin
2: 10 ng standard rat albumin
3: 2 days
4: 2 weeks
5: 3 weeks
6: 5 weeks
7: 6 weeks Time course of human albumin and HBV expression Anti Human Albumin Anti Hepatitis B Surface Antigen 1 week 6 weeks 14 weeks RT-PCR Human Albumin RNA

RT-PCR HBV RNA

1: 1 kbp ladder
2: Rat liver RNA
3: Human liver RNA
4: HepG2.2.15 RNA
5: Rat CA2 — Human hepatocytes + HBV, 1 week post
6: Rat CA2 — 6 weeks post
7: Rat CA2 — 14 weeks post 355 bp 1: 1000 bp ladder
2: Rat RNA
3: Human RNA
4: HepG2.2.15 RNA
5: Rat CA1 — Human hepatocytes + HBV
6: Rat CA2 — Human hepatocytes + HBV
7: Rat CA3 — Human hepatocytes
8: Rat CA4 — Human hepatocytes
9: Rat CA5 — HBV
10: Rat CA6 — HBV
11: Rat CA7 — Saline Hepatocytes plus HBV 1 week Hepatocytes plus HBV 6 weeks Hepatocytes plus HBV 14 weeks Hepatocytes plus HBV 1 week Hepatocytes plus HBV 6 weeks Hepatocytes plus HBV 14 weeks

SEQUENCE LISTING

<160> NUMBER OF SEQ ID NOS: 11

<210> SEQ ID NO 1
<211> LENGTH: 30
<212> TYPE: DNA
<213> ORGANISM: Mus musculus

<400> SEQUENCE: 1
tgtgcttatg tagccatcca gcgagtcccc         30

<210> SEQ ID NO 2
<211> LENGTH: 19
<212> TYPE: DNA
<213> ORGANISM: Hepatitis C virus

<400> SEQUENCE: 2
tcgcgaccca acactactc         19

<210> SEQ ID NO 3
<211> LENGTH: 18
<212> TYPE: DNA
<213> ORGANISM: Hepatitis C virus

<400> SEQUENCE: 3
gggggcgaca ctccacca         18

<210> SEQ ID NO 4
<211> LENGTH: 24
<212> TYPE: DNA
<213> ORGANISM: Homo sapiens

<400> SEQUENCE: 4
ccttggtgtt gattgccttt gctc         24

<210> SEQ ID NO 5
<211> LENGTH: 24
<212> TYPE: DNA
<213> ORGANISM: Homo sapiens

<400> SEQUENCE: 5
catcacatca acctctgtct gacc         24

<210> SEQ ID NO 6
<211> LENGTH: 25

-continued

```
<212> TYPE: DNA
<213> ORGANISM: Ratus ratus

<400> SEQUENCE: 6
atagtgtccc agaaagctgg taggg                                     25

<210> SEQ ID NO 7
<211> LENGTH: 25
<212> TYPE: DNA
<213> ORGANISM: Ratus ratus

<400> SEQUENCE: 7
cggtttaagg acttaggaga acagc                                     25

<210> SEQ ID NO 8
<211> LENGTH: 27
<212> TYPE: DNA
<213> ORGANISM: Hepatitis B virus

<400> SEQUENCE: 8
atcttctgcg acgcggcgat ggagatc                                   27

<210> SEQ ID NO 9
<211> LENGTH: 29
<212> TYPE: DNA
<213> ORGANISM: Hepatitis B virus

<400> SEQUENCE: 9
ctctgctggg gggaattgat gactctagc                                 29

<210> SEQ ID NO 10
<211> LENGTH: 25
<212> TYPE: DNA
<213> ORGANISM: Hepatitis B virus

<400> SEQUENCE: 10
gccggtctgg agcaaagctc atcgg                                     25

<210> SEQ ID NO 11
<211> LENGTH: 24
<212> TYPE: DNA
<213> ORGANISM: Hepatitis B virus

<400> SEQUENCE: 11
ggcggtgtct aggagatctc tgac                                      24
```

PROPAGATION OF HUMAN HEPATOCYTES IN NON-HUMAN MAMMALS

The subject matter herein was generated at least in part under National Institute of Diabetes and Digestive and Kidney Diseases ("NIDDK") Grant No. DK-42182, such that the United States Government has certain rights herein.

1. INTRODUCTION

The present invention relates to the propagation of human hepatocytes in the livers of non-human animals that have been tolerized to the human cells. Such animals provide an in vivo model system of the human liver that may be used in toxicology assays and in the study of human liver diseases, including the various forms of hepatitis (in particular hepatitis B and C) and alcohol-induced liver degeneration. They may also be used as a source of human hepatocytes for reconstitution of liver tissue, thereby providing an alternative to liver transplantation.

2. BACKGROUND OF THE INVENTION

2.1. THE NEED FOR A CULTURE SYSTEM FOR HUMAN HEPATOCYTES

To accurately study the physiology of human liver cells (hepatocytes), scientists need a model system in which the hepatocytes exist as they would in the intact liver. Such systems have proven to be difficult to achieve, because when hepatocytes are removed from their native environment, they tend to lose their specialized functions, or "de-differentiate". The loss of liver-specific functions makes it difficult or impossible to study the normal functions of hepatocytes as well as their response to chemical or biological agents. For example, research directed toward infectious diseases of the liver, in particular viral hepatitis, has been hampered by the lack of an adequate model system. Hepatitis B and hepatitis C, and the problems that have been encountered by scientists studying these infectious and dangerous viruses, are discussed in the following subsections.

In addition, a system for propagating human hepatocytes could be used to provide cells that could be used as an alternative or adjunct to liver transplant. Currently, patients suffering from liver disease may have to wait for long periods of time before a suitable organ for transplant becomes available. After transplant, patients need to be treated with immunosuppressive agents for the duration of their lives in order to avoid rejection of the donor's liver. A method for propagating the patient's own cells could provide a source of functional liver tissue which would not require immunosuppression to remain viable.

2.2 HEPATITIS B VIRUS

Hepatitis B virus ("HBV") is the prototype of the Hepadnaviridae, characterized by a unique genome structure comprising partially double-stranded DNA (*Fields Virology*, 1996, Third Edition, Fields, et al. eds., Lippincott-Raven, New York, pp. 2741–2742). In the United States, there are about a million carriers of HBV, and the number of carriers in the world exceeds 350 million (*Fields Virology*, p. 2741; Petersen et al., 1998, Proc. Natl. Acad. Sci. U.S.A. 95:310–315). In addition to causing an acute hepatitis, viral infection may lead to chronic infection and consequent liver failure and/or the development of hepatocellular carcinoma (*Fields Virology*, pp. 2748–2751). The development of agents that effectively treat and/or prevent the spread of the disease has been limited by the lack of good small animal model systems. Among the models recently developed are a transgenic mouse model and a "Trimera", reported in Petersen et al., 1998, Proc. Natl. Acad. Sci. U.S.A. 95:310–315 and Ilan et al., 1999, Hepatology 29:553–562, respectively.

In the transgenic mouse model of Petersen et al., a transgene encoding a hepatotoxic urokinase-type plasminogen activator was introduced into RAG-2 knockout mice, which lack mature B and T lymphocytes, and then woodchuck hepatocytes were introduced via splenic injection. The woodchuck hepatocytes replaced up to 90 percent of the mouse liver, and supported woodchuck hepatitis virus (another hepadnavirus) replication indefinitely. The replication of the virus responded to pharmacologic agents.

In the Trimera model described by Ilan et al., normal mice were preconditioned by lethal total body radiation, radioprotected with SCID mouse bone marrow cells, and then engrafted with human liver fragments infected ex vivo with hepatitis B.

2.3. HEPATITIS C VIRUS

Hepatitis C virus was first characterized in 1989 (Choo et al., 1989, Science 244: 359–362), but its existence had been posited for many years as an elusive entity that caused flu-like symptoms in certain patients who had received blood transfusions. Because these symptoms were sometimes followed, years later, by liver disease, the clinical syndrome was referred to as non A-non B hepatitis ("NANBH").

Hepatitis C virus ("HCV") is now known to be a member of the Flaviviridae family of viruses, which includes viruses that cause bovine diarrhea, hog cholera, yellow fever, and tick-borne encephalitis (Kato et al., 1990, Proc. Natl. Acad. Sci. U.S.A. 87: 9524–9528; Choo et al., 1991, Proc. Natl. Acad. Sci. U.S.A. 88: 2451–2455; Okamoto et al., 1991, J. Gen. Virol. 72: 2697–2704;Takamizawa et al., 1991, J. Virol. 65: 1105–1113). The viral genome consists of an approximately 9.5 kb single-stranded, positive-sense RNA molecule characterized by a unique open reading frame coding for a single polyprotein (reviewed in Clarke, 1997, J. Gen. Virol 78: 2397–2410 and Major and Feinstone, 1997, Hepatology 25: 1527–1538). Based upon phylogenetic analysis of the core, EI, and NS5 regions, HCV has been found to be genetically heterogeneous, with at least six genotypes and more than 30 subtypes dispersed throughout the world (Major and Feinstone, 1997, Hepatology 25: 1527–1538; Clarke, 1997, J. Genl. Virol 78: 2397–2410).

HCV has been estimated to infect 170 million people worldwide, which is more than four times the number of persons infected with human immunodeficiency virus ("HIV"), and the number of HCV-associated deaths may eventually overtake deaths caused by AIDS (Cohen, 1999, Science 285: 26–30). The Center for Disease Control has calculated that HCV may be harbored by 1.8 percent of the U.S. population. (Id.). The only available therapy is interferon, but most HCV isolates are resistant (Thomas et al., 1999, Hepatology 29: 1333), although more promising results were obtained when interferon was combined with ribavirin (Cohen et al., 1999, Science 285: 26–30 citing Poynard et al., 1998, Lancet 352:1426–1432 and Davis et al., 1998, N. Engl. J. Med. 339:1493–1499). Unfortunately, the interferon/ribavirin combination is less effective against the most common HCV genotype found in the U.S., with only 28 percent of persons infected with that genotype exhibiting a sustained response to treatment. (Davis et al., 1998, N. Engl. J. Med. 339:1493–1499).

The development of more successful forms of therapy (and our understanding of HCV biology) has been hampered by the absence of a good model system for HCV infection. Only humans and certain higher primates are susceptible to infection (Feinstone et al., 1981, J. Infect. Dis. 144: 588). A variety of mammalian cell systems which support the growth of HCV have been reported which rely on the use of strand-specific RT-PCR as evidence of virus replication (Major and Feinstone, 1997, Hepatology 25:1527–1538 citing Mitzutani et al., 1995, Biochem. Biophys. Res. Commun. 212: 906–911; Shimizu and Yoshikura, 1994, 68: 8406–8408; Kato et al., 1995, Biochem. Biophys. Res. Commun. 206: 863–869; Cribier et al., 1995, J. Gen. Virol. 76: 2485–2491; and Yoo et al., 1995, J. Virol. 69: 32–38).

As reviewed in Clarke (supra), there have been reports of viral replication in systems based on hepatic tissue (Ito, et al., 1996, J. Gen. Virol. 77: 1043–1054), peripheral blood mononuclear cells (Willems et al., 1996, J. Med. Virol. 42: 272–278; Zignego et al., 1992, J. Hepatology 15: 382–386), human T and B cell lines (Bertolini et al., 1993, Res. Virol 144: 281–285; Shimizu et al., 1992, Proc. Natl. Acad. Sci. U.S.A. 89: 5477–5481), human fetal liver cells (Iacovacci et al., 1993, Res. Virol. 144: 275–279), chimpanzee hepatocytes (Lanford et al., 1994, Virol. 202: 606–614), Daudi B-cells (Nakajima et al., 1996, J. Virol. 70: 3325–3329), and the human T cell leukemia virus type I-infected T cell line MT-Z (Mitzutani et al., 1995, Biochem. Biophys. Res. Comm. 212: 906–911; Sugiyama et al., 1997, J. Gen. Virol. 78: 329–336). None of these systems has, however, proved satisfactory.

Hepatitis C infected human liver tissue was transplanted into Trimera mice described in the preceding section, as reported by Galun et al., 1995, J. Infect. Dis. 172:25–30.

A newer system was recently reported by Lohmann et al. (1999, Science 285: 110–113) in which subgenomic HCV RNA replicons were transfected into a human hepatoma cell line and found to replicate to high levels. Nonetheless, this system does not generate virus and therefore is not a model of productive infection (Cohen, supra).

2.3. HEPATOCYTES FOR LIVER RECONSTITUTION

Reconstitution of liver tissue in a patient by the introduction of hepatocytes (also referred to as "hepatocyte transplantation") is a potential therapeutic option for patients with acute liver failure, either as a temporary treatment in anticipation of liver transplant or as a definitive treatment for patients with isolated metabolic deficiencies (Bumgardner et al., 1998, Transplantation 65: 53–61). Animal models have been developed for studying the effectiveness of hepatocyte transplantation in the context of pharmacologically or surgically induced liver failure (Id, citing Mito et al., 1993, Transplant Rev. 7: 35; Takeshita et al. 1993, Cell Transplant 2: 319; Sutherland et al., 1977, Surgery 82: 124; Sommer et al., 1979, Transplant Proc. 9: 578; and Demetriou et al., 1988, Hepatology 8: 1006), or for the treatment of isolated errors of metabolism (Wiederkehr et al., 1990, Transplant 50: 466; Onodera et al., 1995, Cell Transpl. 4 (Supp. 1): 541; Cobourn et al., 1987, Transpl. Proc. 19: 1002; Rozga et al., 1995, Cell Transplant 4: 237; Kay et al., 1994, Hepatology 20: 253; Matas et al., 1976, Science 192: 892; Holzman et al., 1993, Transplantation 55: 1213; Moscioni et al., 1989, Gastroenterol. 96: 1546; Groth et al., 1977, Transplant Proc. 9: 313). Use of transfected hepatocytes in gene therapy of a patient suffering from familial hypercholesterolemia has been reported in Grossman et al., 1994, Nat. Genet. 6: 335.

A major obstacle to achieving therapeutic liver reconstitution is immune rejection of transplanted hepatocytes by the host, a phenomenon referred to (where the host and donor cells are genetically and phenotypically different) as "allograft rejection". Immunosuppressive agents have been only partially successful in preventing allograft rejection (Jauregui et al., 1996, Cell Transplantation 5: 353–367, citing Darby et al., 1986, Br. J. Exp. Pathol. 67: 329–339; Maganto et al., 1988, Eur. Surg. Res. 20: 248–253; Makowka et al., 1986, Transplantation 42: 537–541). The three main alternative approaches which have been explored are 1) physically shielding transplanted cells from the host immune system, for example, in an alginate-polylysine or chitosan capsule; 2) depletion of antigen presenting cells; or 3) induction of alloantigen-specific tolerance in the host (Jauregui et al., supra). Chowdhury has tested the hypothesis that intrathymic injection of donor rat splenocytes may result in suppression of allograft hepatocyte rejection in peripheral lymphocyte depleted adult rats (Jauregui et al., supra, citing Fabrega et al., 1995, Transplantation 59: 1362–1364). In that study long-term tolerization occurred with administration of splenocytes but not hepatocytes.

For successful reconstitution, the age of the donor cells has been considered significant. Cusick et al. (1997, J. Ped. Surg. 32: 357–360) report that transplanted fetal hepatocytes had a significant survival advantage over adult hepatocytes, independent of recipient age. However, Rhim et al. (1994, Science 263: 1149–1152) demonstrated that adult mouse liver cells could proliferate when introduced into the livers of congenic transgenic mice carrying a hepatotoxic transgene (urokinase under the control of the albumin promoter, which is liver-specific and only active postnatally). The donor cells were observed to have divided at least 12 times (reconstitution of an entire liver from one hepatocyte would require 28 cell doublings).

3. SUMMARY OF THE INVENTION

The present invention relates to the preparation of tolerized non-human animals having chimeric livers, wherein some or a majority of the hepatocytes present are human hepatocytes. It is based, at least in part, on the discovery that rats, tolerized in utero against human hepatocytes, were found to serve as long-term hosts for human hepatocytes introduced postnatally, and that the introduced hepatocytes maintained their differentiated phenotype, as evidenced by continued production of human albumin.

In a first embodiment, the present invention provides for a method of preparing a non-human animal having a liver comprising human hepatocytes, comprising (i) inducing tolerance in an immunocompetent host non-human animal, where the animal is preferably a fetus or a neonate; and (ii) introducing human hepatocytes into the tolerized animal, preferably postnatally and preferably by intra-splenic injection. In specific non-limiting embodiments, the host animal is subjected to a selection pressure which favors survival and/or proliferation of human, rather than host animal, hepatocytes.

In a second embodiment of the invention, an animal having a chimeric liver, prepared as described above, may be used as a model system for human hepatocyte function in a toxicology study. Because the human hepatocytes maintain their differentiated state and are situated in their natural anatomic location, this model system recapitulates the metabolic fate of test agents as they pass from the site of administration through the liver.

In a third embodiment of the invention, an animal having a chimeric liver may be used as a model system for human liver disease. Such model systems are particularly useful for diseases which specifically effect human (or primate), but not non-human (or non-primate) livers, such as hepatitis B and hepatitis C infection and alcohol-induced liver degeneration/fibrosis. Immunocompetent chimeric animals of the invention exhibit the further advantage of having an immune system which is intact but for exhibiting tolerance toward the human cells comprised in the animal's liver.

In a fourth embodiment of the invention, an animal having a chimeric liver may be used as a source of human hepatocytes which may be used therapeutically. As non-limiting examples, such human hepatocytes may be used in gene therapy applications or to reconstitute liver tissue in a human host whose own liver has been substantially damaged. Large animals having a chimeric liver may be particularly desirable for such embodiments.

The file of this patent contains seven drawings executed in color. Copies of this patent with color drawings will be provided by the Patent and Trademark Office upon request and payment of the necessary fee.

4. DESCRIPTION OF THE FIGURES

FIG. 1. $^3$[H]-thymidine incorporation in mixed lymphocyte assays where the responder cells were rat spleen cells and the stimulator cells were irradiated human hepatocytes. "Spleen (iu)" designates spleen cells from rats tolerized by intrauterine injection of human hepatocyte lysates, and "spleen (iu/is)" designates spleen cells from rats tolerized as fetuses with human hepatocyte lysates followed by intrasplenic transplantation of human hepatocytes after birth.

Figure 2:
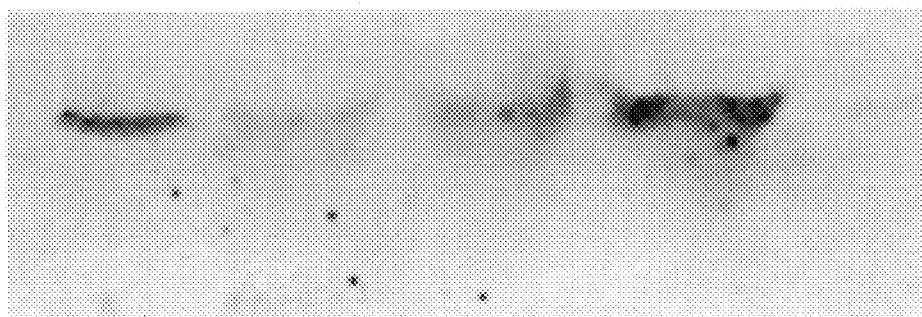

FIG. 2. Western blot, using anti-human albumin antibody as a probe, of human serum albumin (lane 1), serum from a tolerized rat six weeks after intrasplenic injection (lane 2), and sera from a tolerized rat, injected with human hepatocytes, 24 hours (lane 3), and eight days (lane 4) after a second injection of human hepatocytes. Lane 5 contains serum from a non-tolerized rat eight days after a second injection of human hepatocytes.

Figure 3:
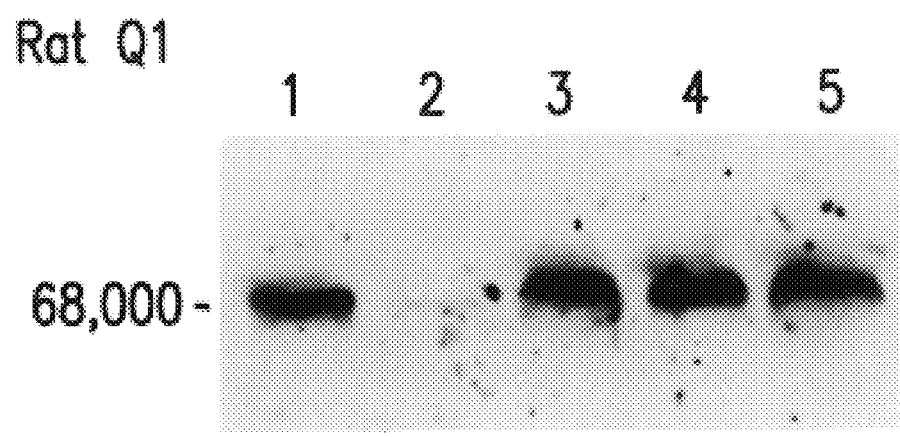

FIG. 3. Western blot, using anti-human albumin antibody as a probe, of human serum albumin (lane 1), rat serum albumin (lane 2), and serum from a tolerized rat that had received an intrasplenic injection of human hepatocytes, one week (lane 3), two weeks (lane 4) and three weeks (lane 5) after injection with human hepatocytes.

FIGS. 4A–D. Immunofluorescence studies using anti-human albumin as primary antibody and fluorescent Texas red-coupled secondary antibody. (A) Anti-human albumin antibody binding to control (non-chimeric) rat liver; (B) anti-human albumin antibody binding to chimeric rat liver three weeks after injection with human hepatocytes; (C) same as B, without secondary antibody visualization; and (D) anti-human albumin antibody binding to the liver of a rat that had been tolerized with a human hepatocyte lysate but did not receive subsequent injection of viable liver cells.

Figure 4A:
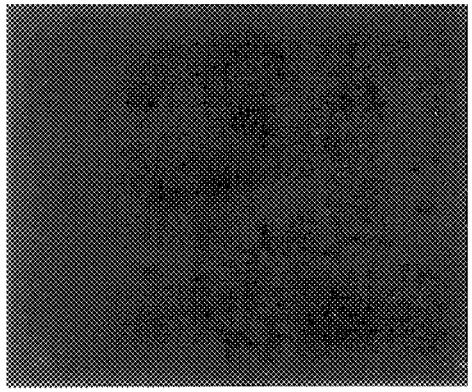
Figure 4B:
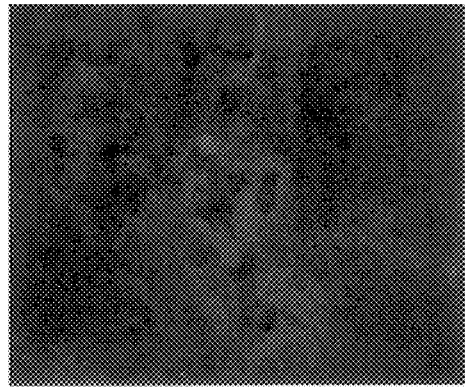
Figure 4C:
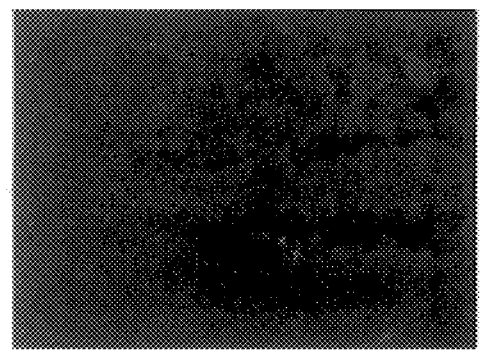
Figure 4D:
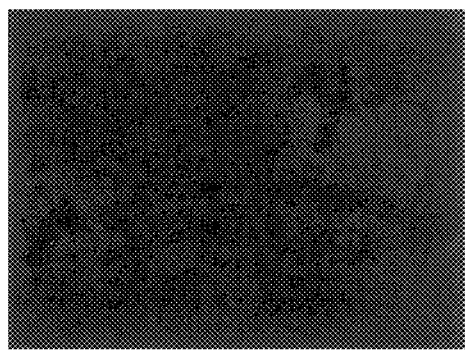
Figure 5:
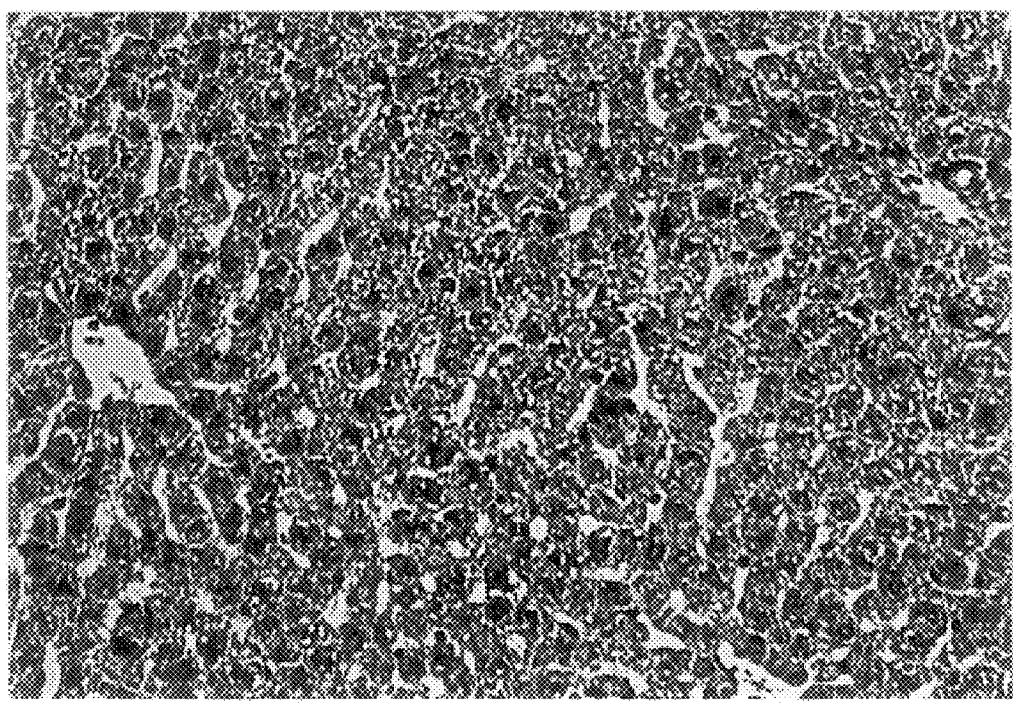
Figure 6A:
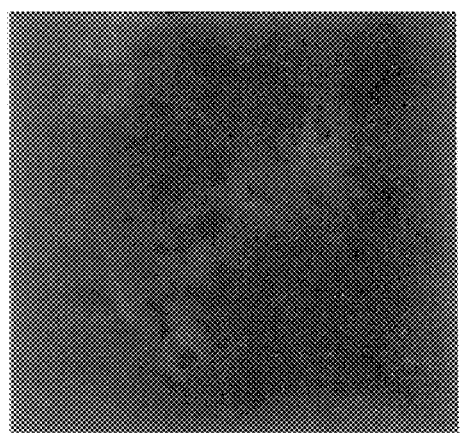
Figure 6B:
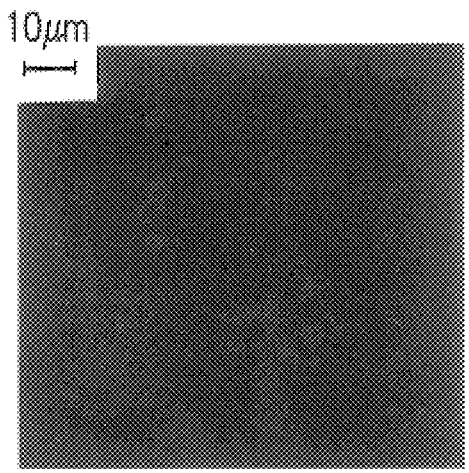
Figure 6C:
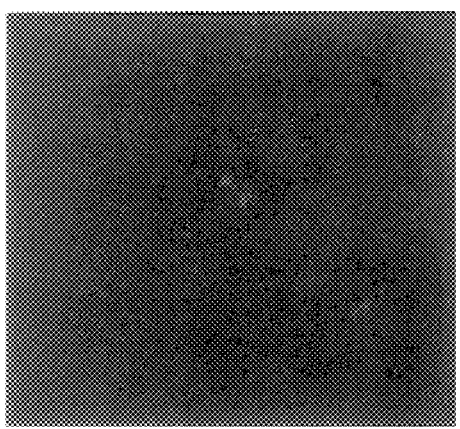
Figure 6D:
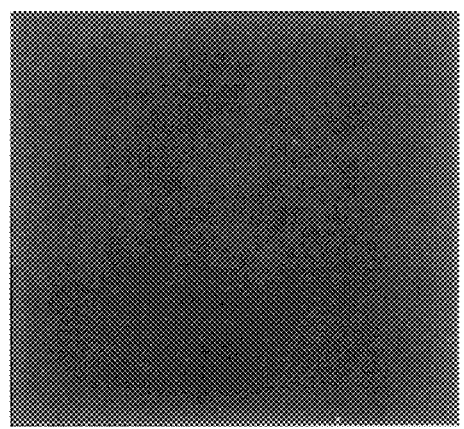

FIG. 5. The same section of chimeric rat liver shown in FIG. 4B to express human albumin, stained with hematoxylin and eosin to demonstrate normal histology.

FIGS. 6A–D. Immunofluorescence studies using primary and secondary antibodies as in FIG. 4A–D, showing (A) a section of liver from a tolerized rat six weeks after intrasplenic injection with human hepatocytes, stained with both antibodies; (B) as in (A), but without secondary antibody staining; (C) as in (A), but with no antibody binding; and (D) a section of liver from a non-tolerized rat, six weeks after intrasplenic injection of human hepatocytes, stained with both antibodies.

Figure 7:
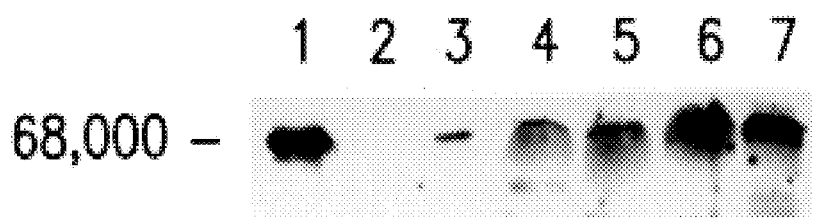

FIG. 7. Western blot, using anti-human albumin antibody as a probe, of human serum albumin (lane 1), rat serum (lane 2) and sera from a chimeric rat which had been tolerized by intrathymic injection of human hepatocytes, at varius times after intrasplenic injection with human hepatocytes (lane 3=2 days, lane 4=2 weeks, lane 5=3 weeks, lane 6=5 weeks, lane 7=6 weeks).

FIGS. 8A–F. Immunofluorescence studies of liver sections from tolerized rats injected with human hepatocytes and inoculated with hepatitis B virus (HBV) at 1 week, 6 weeks, and 14 weeks following inoculation, stained with anti-albumin primary and Texas red conjugated secondary antibody (FIGS. 8A, 8C and 8E, for weeks 1, 6 and 14, respectively) or anti-hepatitis B surface antigen (HBsAg) antibody and FITC-conjugated secondary antibody (FIGS. 8B, 8D, and 8F for weeks 1, 6 and 14, respectively).

Figures 9A, 9B:
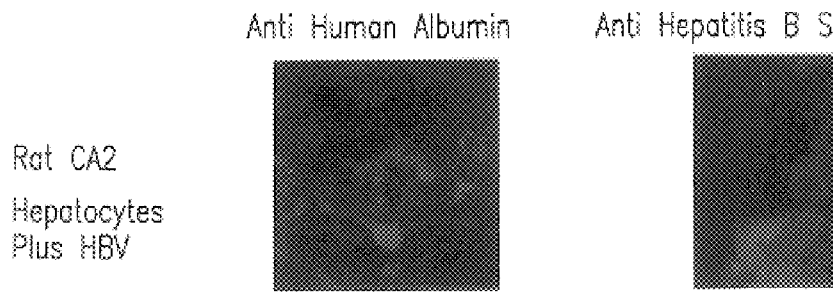
Figures 9C, 9D:
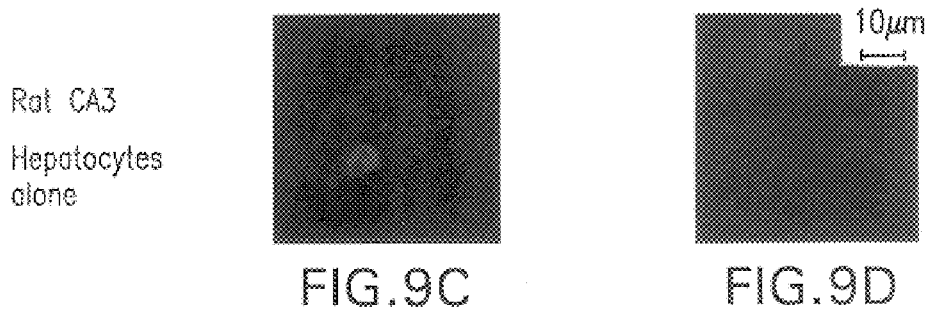
Figures 9E, 9F:
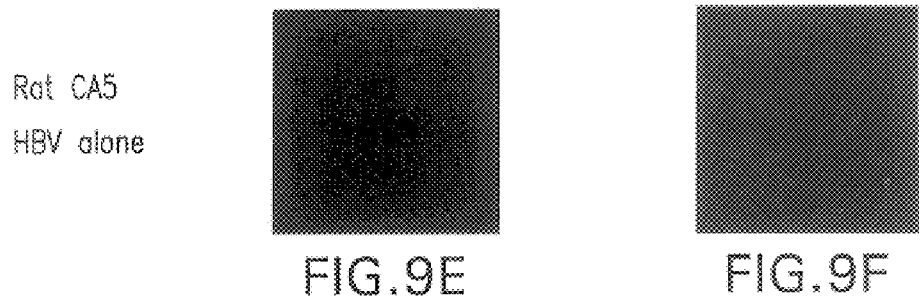
Figures 9G, 9H:
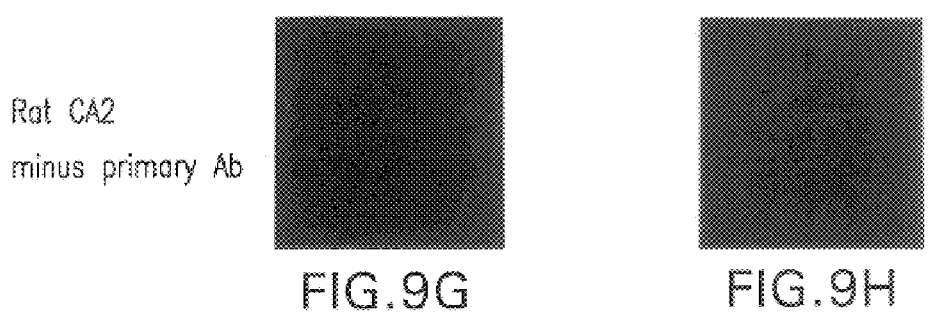

FIGS. 9A–H. Immunofluorescence studies of liver sections from rats that were either (i) tolerized, injected with human hepatocytes, and inoculated with HBV (CA2)(FIGS. 9A and 9B); (ii) tolerized and injected with human hepatocytes but not inoculated (CA3) (FIGS. 9C and 9D); (iii) tolerized and inoculated with HBV, without injection of human hepatocytes (CA5) (FIGS. 9E and 9F); or tolerized, injected with human hepatocytes and inoculated with HBV (CA2) but not reacted with primary anti-albumin or anti-HBsAg antibodies (FIGS. 9G and 9H). Sections were stained with anti-albumin primary and Texas red conjugated secondary antibody (FIGS. 9A, 9C, 9E, and 9G) or anti-HBsAg antibody and FITC-conjugated secondary antibody (FIGS. 9B, 9D, 9F, and 9H).

Figure 10:
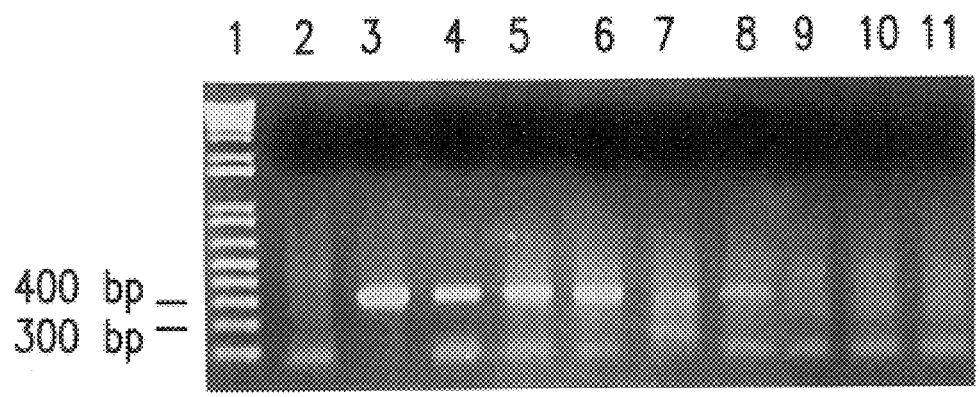

FIG. 10. Photograph of an ethidium bromide stained gel of products of RT-PCR of human albumin mRNA, the lanes containing the RT-PCR products resulting from experiments using, as template, RNA from: lane 2=rat; lane 3=human; lane 4=HepG2.2.15; lane 5=Rat CA1 (tolerized, injected with human hepatocytes, subsequently inoculated with HBV); lane 6=Rat CA2 (tolerized, injected with human hepatocytes, subsequently inoculated with HBV); lane 7=rat CA3 (tolerized and injected with human hepatocytes but not inoculated with HBV); lane 8=rat CA4 (tolerized and injected with human hepatocytes but not inoculated with HBV); lane 9=(tolerized and inoculated with HBV, without injection of human hepatocytes); lane 10=(tolerized and inoculated with HBV, without injection of human hepatocytes); lane 11=rat CA7 (treated with saline, negative control); and where lane 1=1,000 bp ladder.

Figure 11A:
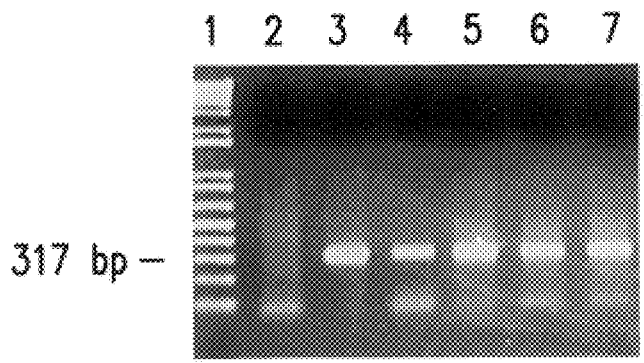
Figure 11B:
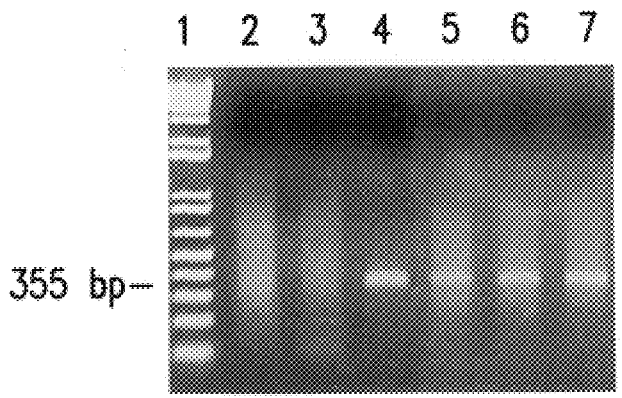

FIGS. 11A–B. Photograph of an ethidium bromide stained gel of products of RT-PCR of human albumin mRNA (FIG. 11A) and HBV RNA (FIG. 11B), the lanes containing the RT-PCR products resulting from experiments using, as template, RNA from: lane 2=rat; lane 3=human; lane 4=HepG22.2.15; lane 5=Rat CA2 (tolerized, injected with human hepatocytes, inoculated with HBV) 1 week post-inoculation; lane 6=Rat CA2 6 weeks post-inoculation; lane 7=rat CA2 14 weeks post-inoculation, where lane 1=1,000 bp ladder.

Figure 12:
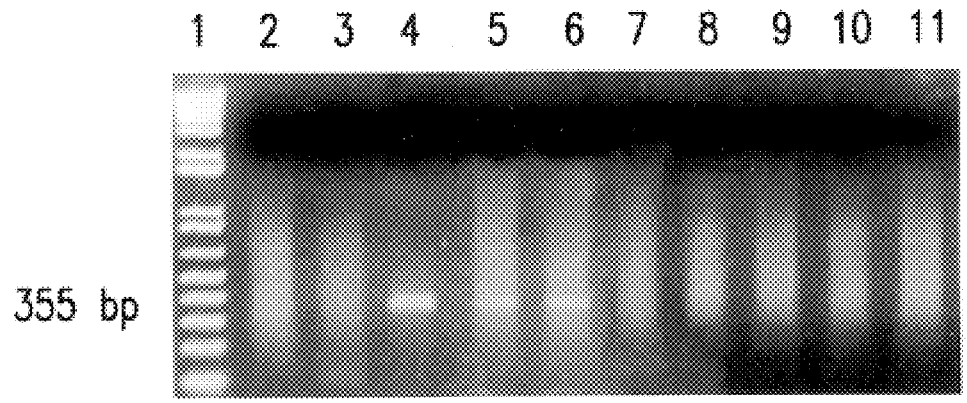

FIG. 12. Photograph of an ethidium bromide stained gel of products of RT-PCR of human hepatitis B viral RNA, the lanes containing RT-PCR products resulting from experiments using, as template, RNA from: lane 2=rat; lane 3=human; lane 4=HepG22.2.15; lane 5=Rat CA1 (tolerized, injected with human hepatocytes and inoculated with HBV); lane 6=Rat CA2 (tolerized, injected with human hepatocytes, inoculated with HBV); lane 7=Rat CA3 (tolerized with human hepatocytes but not inoculated with HBV); lane 8=Rat CA4 (tolerized with human hepatocytes but not inoculated with HBV); lane 9=Rat CA5 (tolerized with human hepatocytes, not injected with human hepatocytes, inoculated with HBV); lane 10=Rat CA6 (tolerized with human hepatocytes, not injected with human hepatocytes, inoculated with HBV); where lane 1=1,000 bp ladder.

Figure 13A:
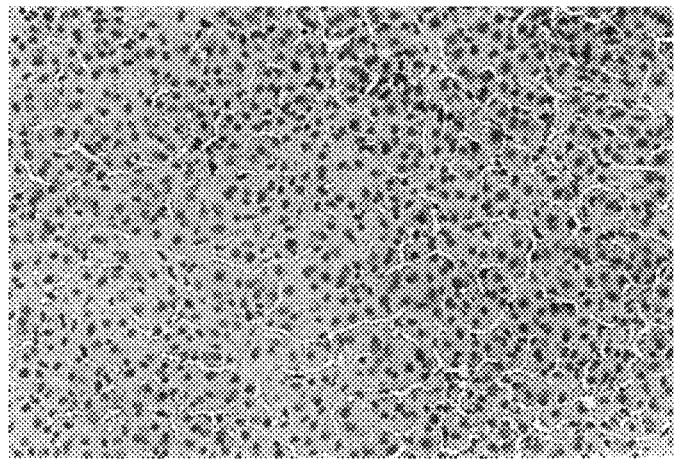
Figure 13B:
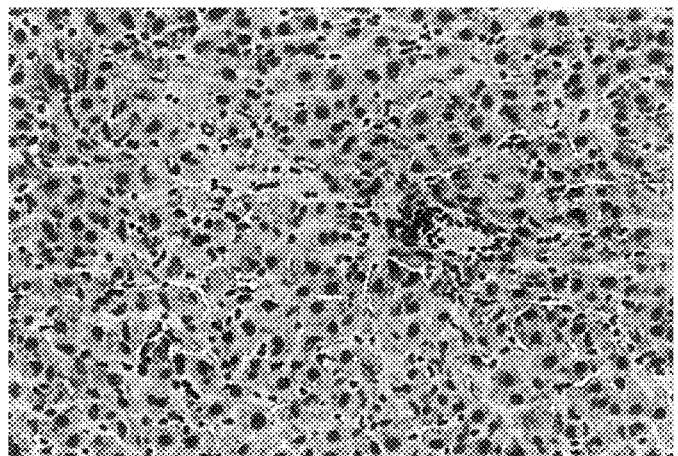
Figure 13C:
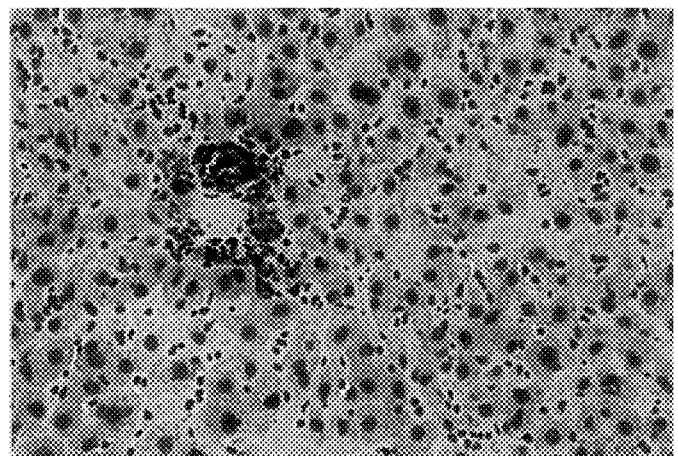

FIGS. 13A–C. Photomicrographs of hematoxylin-eosin stained liver sections, at low (20x) magnification, of liver sections from a rat tolerized, transplanted with human hepaotcytes, and inoculated with HBV, (13A) 1 week, (13B) 6 weeks, or (13C) 14 weeks post-inoculation.

Figure 14A:
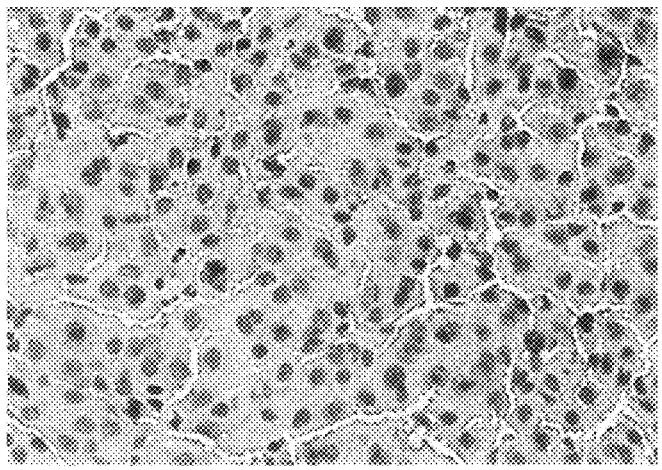
Figure 14B:
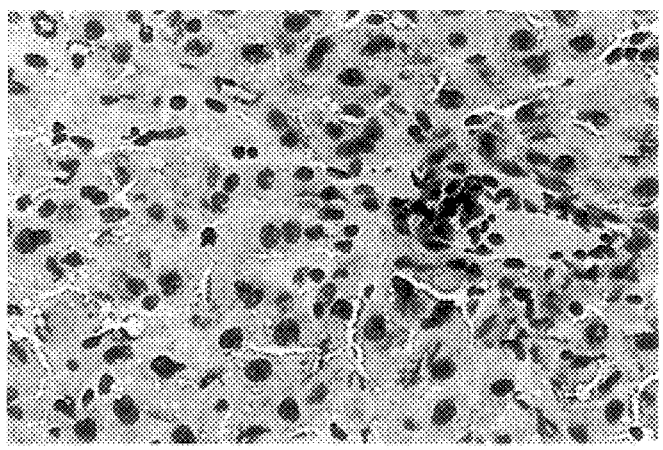
Figure 14C:
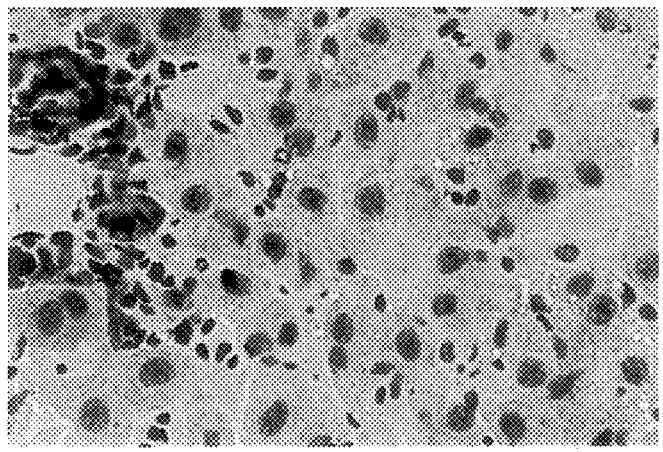

FIGS. 14A–C. Photomicrographs of hematoxylin-eosin stained liver sections, at high (40x) magnification, of liver sections from a rat tolerized, transplanted with human hepaotcytes, and inoculated with HBV, (13A) 1 week, (13B) 6 weeks, or (13C) 14 weeks post-inoculation.

5. DETAILED DESCRIPTION OF THE INVENTION

The present invention relates to tolerized non-human animals having chimeric livers comprising human hepatocytes, methods for preparing such animals, and the use of such animals either as model systems for assaying toxicology or studying human liver disease or as sources of human hepatocytes for re-introduction into a human host. For purposes of clarity, the description of the invention is presented as the following subsections:

i) producing animals having chimeric livers;

ii) toxicology model systems;

iii) model systems for liver diseases; and iv) chimeric animals as a source of hepatocytes for liver reconstitution.

The subject animals of the invention are referred to herein alternatively as "non-human animals having chimeric livers" or simply "chimeric animals". Both these terms are defined as tolerized non-human animals having livers which comprise human hepatocytes. In addition to the human hepatocytes, the livers of the chimeric animals may also include hepatocytes and non-hepatocyte elements (e.g., biliary and vascular endothelial cells, Kupffer cells, etc.) endogenous to the animal itself Human cell types other than hepatocytes may also be present. Preferably, the percentage of human hepatocytes (relative to the total number of hepatocytes present) is at least 10 percent, more preferably at least 20 percent, or at least 50 percent, or at least 80 percent.

In particular, chimeric animals are created by introducing human hepatocytes (and possibly additional cell types) into an animal rendered immunologically tolerant to the introduced human cells. As such, the animals may be referred to as being "hosts" to the human cells, where a human being that is a source of such cells may be referred to as a "donor". The term "tolerant", as used herein, does not refer to a state of general immunosuppression (as might be achieved, for example, by treatment with cyclosporine, or as may exist in an animal with a generalized B cell and/or T cell deficiency) but rather indicates a state of antigen-induced non-responsiveness of lymphocytes achieved by clonal deletion, cell-mediated suppression, or anergy (see, for example, Davies, 1997, "Introductory Immunobiology", Chapman & Hall, London, p. 366) directed specifically toward the introduced human cells.

5.1. PRODUCING ANIMALS HAVING CHIMERIC LIVERS

The present invention provides for a method of preparing a non-human animal having a liver comprising human hepatocytes, comprising (i) inducing tolerance in a host animal, where the animal is preferably a fetus or a neonate; and (ii) introducing human hepatocytes into the tolerized animal, preferably postnatally and preferably by intrasplenic injection. In specific embodiments, the host animal is subjected to a selection pressure which favors survival and/or proliferation of human, rather than host animal, hepatocytes. A detailed non-limiting description of these features of the invention is set forth in the following subsections.

5.1.1. HOST ANIMALS

Non-human animals which may serve as hosts according to the invention are preferably mammals, and include, but are not limited to, mice, hamsters, rats, rabbits, dogs, goats, sheep, pigs, cattle, etc. In particular non-limiting embodiments of the invention, the host animal is a transgenic animal carrying, as a transgene, a gene which, when expressed in hepatocytes, is directly or indirectly (i.e. via a metabolite) toxic to those cells. Examples of such genes are the urokinase gene which is directly toxic (Sandgren et al., 1991, Cell 66:245), and the Herpes simplex virus ("HSV") thymidine kinase gene ("HSV-TK"); which converts the drug gancyclovir into a toxic form and is therefore indirectly toxic (Smythe et al., 1995, Ann. Surg. 222:78–86). Preferably, the gene is operably linked to a promoter which is selectively active in hepatocytes, such as the albumin promoter, the PEPCK promoter, and the hepatitis B surface antigen promoter. To avoid destroying the animal's liver prior to colonization with human hepatocytes, it is desirable to utilize a promoter that is not particularly active prenatally. Otherwise, such transgenic animals may die in utero. Other promoters inducible by agents that could be locally administered into the liver may also be suitable, such as the metallothionein promoter (which is inducible by heavy metal ions; Palmiter et al., 1982, Cell 29:701). Such genes are not specifically toxic to human hepatocytes, although there may be some "bystander effect" whereby a limited number of the human hepatocytes are killed.

In one specific, non-limiting embodiment of the invention, transgenic mice carrying an albumin promoter/urokinase transgene may be used as hosts. Urokinase is a plasminogen activator that is useful clinically in dissolving blood clots. When introduced into hepatocytes by an adenoviral vector, it was shown to be toxic to those cells (Lieber et al., 1995, Proc. Natl. Acad. Sci. U.S.A. 92:6210–6214). In addition, Sandgren et al. prepared a transgenic mouse containing the mouse urokinase gene driven by a mouse albumin enhancer/promoter (Sandgren et al., 1991, Cell 66:245–256). Because albumin is not produced by the fetal liver (Krumlauf et al., 1985, Cold Spring Harbor Symp. Quant. Biol. 5-0:371–378), animals survived in utero because urokinase was not produced. However, after birth, with activation of the albumin promoter, the liver was destroyed due to the presence of urokinase. To produce such a transgenic mouse for use as a host, heterozygote transgenic mice, B6SJL background, may be obtained from Jackson Laboratories, Stock No. 002214, which contain the mouse urokinase gene driven by a 3.5 kb mouse albumin promoter sequence with a human growth hormone poly A addition site. Pregnant mice from heterozygotic matings may be used to generate homozygous offspring. The number of copies of the urokinase transgene present in each animal at birth may be determined from DNA extracts of tail snips, where the DNA may be digested with Kpn 1, which cuts once within the urokinase gene, and Southern blotting using a detectably labeled probe specific for the urokinase gene, such as 5'-TGTGCTTATG TAGCCATCCA GCGAGTCCCC-3' (SEQ ID NO: 1). Because somatic mutations leading to inactivation of the urokinase gene may occur, it may be desirable to use breeding pairs of male and female mice successfully rescued into adulthood by introduction of human hepatocytes to generate litters of homozygous offspring. Further, in previous studies on mice carrying a urokinase transgene, inactivating mutations in the urokinase gene were found to result in proliferation of those cells with that somatic mutation while the homozygous cells failed to grow. The proliferating cells, as expected, had higher ploidy than those less actively proliferating (Sandgren et al., 1991, Cell 66:245–256). Thus, the copy number of human DNA, if measured during proliferation of human hepatocytes may be biased, and not reflect the number of cells due to polyploidy. For this reason, the number of human cells may be better estimated by measuring markers specific for human hepatocytes, such as, but not limited to, the human albumin gene or its protein product.

In another specific non-limiting embodiment of the invention, transgenic mice carrying an albumin promoter/HSV-thymidine kinase gene may be used as hosts. Thymidine kinase of HSV differs from mammalian thymidine kinases in its ability to phosphorylate the drug gancyclovir (Fyfe et al., 1978, J. Biol. Chem. 253:8721–8727). In so doing, it converts the non-toxic agent into a toxic form (De Clerq, 1984, Biochem. Biopharmacol. 33:2159–2169). In a specific non-limiting embodiment, the HSV-TK gene (as present in plasmid pLTR-DTK, as developed by D. Klatzmann, Universite Pierre et Marie Curie, Paris, France) may be linked to an albumin promoter prepared by excising a 3.2 kb fragment of the mouse albumin promoter (for example from palb$_{9-12}$LDLR, James Wilson, University of Pennsylvania, Philadelphia, Pa.) using Bgl II and Sal 1 restriction enzymes (Wilson et al., 1992, J. Biol. Chem. 267:963–967), and placing the promoter fragment in a polylinker site immediately upstream of the HSV-TK gene. Using this plasmid, founder outbred CD1 mice may be prepared and mated to normal CD1 mice to generate heterozygotes, detected by DNA analysis of tail snips using an HSV-TK specific detectably labeled probe. A breeding pair of heterozygotes may then be used to produce mice homozygous for the albumin promoter/HSV-TK transgene. It should be noted that the natural HSV-TK gene contains elements that activate the gene in the testes, which may result in sterile animals that cannot be used as breeders. Accordingly, a version of the gene which lacks these elements is preferred, such as the gene contained in plasmid pLTR-ΔTK (all such variant genes, as well as the wild-type, are considered HSV-TK genes). Breeding of transgenic mice with this specific construct confirmed the success of the deletion (Salomon et al., 1995, Mol. Cell. Biol. 15:5322–5328). Further, a gancyclovir dose-related (Culver et al., 1992, Science 256:1550–1552) bystander effect of the HSV-TK gene product has been observed whereby nearby cells lacking the transgene are destroyed (Kolberg, 1994, J. NIH Res. 6:62–64). Accordingly, it may be desirable to evaluate different doses of gancyclovir and identify the minimum dose required to produce maximal human hepatocyte proliferation.

5.1.2. TOLERIZATION

Non-human animals which are to be used as hosts for human hepatocytes may be rendered tolerant to those hepatocytes by administration of the relevant antigen(s), preferably in the context of human cells or a lysate prepared from human cells, more preferably using human cells from the same individual who is to serve as the hepatocyte donor. Tolerizing antigen(s) may be administered as whole cells, a cell extract or one or more purified component thereof. The source of tolerizing antigen(s) may be hepatocytes, but may alternatively be cells of another type, or a mixture of different types of cells. For example, cells prepared from a specimen of human liver tissue may be used as a source of tolerizing antigen(s); such cells may include not only hepatocytes but also fibroblasts, cells of the biliary system, vascular endothelial cells, Kupffer cells, etc. As another example, human splenocytes or lysates thereof may be used to induce tolerance. Cells to be used in tolerization are preferably cleared of undesirable constituents. For example, if the animal is eventually to be used as a model system for a disease where an immune response to an infectious agent is desirably left intact, the animal should not be tolerized against the infectious agent. Alternatively, if the animal is to be used as a host to support the proliferation of human hepatocytes to be used to reconstitute the liver of a person having liver damage caused by an infectious agent, it is desirable not to tolerize the host animal toward the infectious agent or to introduce the infectious agent into the host animal at any time. The cells or lysate are introduced in a physiologically compatible solution; herein, volumes administered refer to cells or lysate comprised in such a solution.

While the host animal may potentially be of any age when tolerized, tolerization is likely to become more difficult as age of the animal increases. Preferably, the animal is still an infant when tolerized; more preferably, the animal is a neonate, or tolerized in utero. If the intended host animal is a rat, the preferable upper age limit for tolerization is 18 days post-conception (in utero), and the more preferable age for tolerization is 17 days post-conception (in utero), or within 24 hours after birth. If the intended host animal is a mouse, the preferable upper age limit for tolerization is 18 days post-conception (in utero), and the more preferable age for tolerization is 17 days post-conception (in utero), or within 24 hours after birth. If the intended host animal is a pig, the preferable upper age limit for tolerization is 90 days post-conception, and the more preferable age for tolerization is 80 days post-conception, when the animal is still in utero, or within 24 hours after birth.

Tolerization may be accomplished by any route, including but not limited to intravenous, intraperitoneal, subcutaneous, and intrathymic routes. Preferred methods of tolerization include inoculation of human cells into the thymus or intraperitoneally.

As a specific, non-limiting example, where the intended host animal is a rat, tolerance may be induced by inoculating lysate prepared from $1\times10^4$–$1\times10^6$ and preferably $0.5 \times 10^5$ human hepatocytes into the peritoneum of a 15–18 day old, and preferably a 17 day old, rat fetus in utero under transillumination. The lysate may be prepared by sonicating a suspension of the appropriate number of human hepatocytes. The same numbers of whole cells may also be inoculated into the peritoneum during the aforesaid time periods. If the intended host animal is a mouse, the number of human hepatocytes represented in the lysate may be $1\times10^3$–$1\times10^5$ and preferably $10^4$ and intraperitoneal inoculation may be performed between days 15 and 18 post conception. If the intended host animal is a pig, the number of human hepatocytes represented in the lysate may be between about $10^5$ and $10^6$ or the same number of whole cells and intraperitoneal inoculation may be performed at between about 75 and 90 days post-conception. Alternatively, intraperitoneal inoculation can be performed while the animals are neonates.

As a second non-limiting example, tolerance may be induced by intrathymic injection according to a method as described in Fabrega et al., 1995, Transplantation 59:1362–1364. Either whole cells or a cell lysate may be administered. In particular, where the intended host animal is a rat, about $1\times10^2$–$1\times10^4$, preferably 100, human hepatocytes (or a lysate thereof) in between about 1 and 10 microliters, preferably about 5 microliters, may be injected into the thymus of a newborn (neonatal) rat, preferably within 1–2 hours of birth. Where the intended host animal is a mouse, about $1\times10^2$–$1\times10^4$ and preferably 100 human hepatocytes (or a lysate thereof) in between about 1 and 10 microliters and preferably about 5 microliters may be injected into the thymus of a mouse that is up to 3 months old and preferably a neonate, e.g. within 1–2 hours or within 24 hours of birth. Where the intended host animal is a pig, about $10^5$–$10^6$ human hepatocytes (or a lysate thereof) in between about 50 and 200 microliters may be injected into the thymus of an infant pig that is preferably up to one week old. As a specific example, a neonatal mouse may be anesthetized by chilling on ice, the thoracic area may be cleaned with alcohol and betadine swipes, the thymus may be visualized through the translucent skin of the newborn, and a 1–2 mm incision may be made with ophthalmic scissors to expose the thymus. The human cells or human cell lysate may then be slowly injected into the thymus, and then the incision may be closed with a sterile nylon suture. The incision area may then be recleaned and the mouse placed on a warming pad and returned to its mother as soon as possible.

The success of tolerization may be assessed by proceeding to introduce human hepatocytes into the animal, and determine whether or not they survive long-term (for example, by monitoring the production of human serum albumin; see infra). Alternatively, the ability of lymphocytes from the animal to react with donor human hepatocytes may be evaluated using standard immunologic techniques, such as methods that determine T cell proliferation in response to donor hepatocytes, the induction of a cytotoxic T cell response, or mixed lymphocyte reaction.

5.1.3. INTRODUCTION OF HUMAN LIVER CELLS

Human liver cells may then be introduced into host animals rendered tolerant as set forth in the preceding section. The hepatocytes may preferably be introduced via intrasplenic injection, although other routes may also be used, such as direct injection into the liver parenchyma, under the liver capsule, or via the portal vein.

As a specific non-limiting example, where the intended host animal is a rat tolerized as set forth above, between about $10^6$–$5\times10^7$ human hepatocytes, preferably about $2\times10^6$ hepatocytes, may be introduced into a tolerized rat within about 24 hours after birth by anesthetizing the animal, making a 3–4 mm incision in the left paracostal area to visualize the spleen (Marucci et al., 1997, Hepatol. 26:1195–1202), and injecting the donor cells in a volume of approximately about 50–300 microliters, and preferably about 200 microliters, of sterile medium. Where the intended host animal is a tolerized mouse, the number of human hepatocytes introduced by an analogous procedure may be between about $5\times10^3$ and $5\times10^6$, preferably about $10^5$ in a volume of about 25–200 microliters, and preferably about 100 microliters, of sterile medium, and the human hepatocytes are administered between about one day and two months, preferably 3–4 days, after tolerization. Where the intended host animal is a tolerized pig, the number of human hepatocytes may be between about $10^8$–$10^{10}$, preferably about $10^9$, in a volume of about 10–20 milliliters of sterile medium and the human hepatocytes are administered about one and seven days after birth or about 35 days after tolerization.

Human hepatocytes may be obtained from a commercial source, for example, Clonetics Corporation, 8830 Biggs Ford Road, Walkersville, Md. 21793, which sells normal human hepatocytes as catalog number CC-2591.

Alternatively, human hepatocytes may be prepared from a donor as follows. The source of cells may be from a liver biopsy taken percutaneously or via abdominal surgery, or from liver tissue obtained postmortem. The source of cells should be maintained in a manner which protects cell viability. In one specific non-limiting embodiment, human hepatocytes may be prepared using the technique described in Guguen-Guillouzo et al., 1982, "High yield preparation of isolated human adult hepatocytes by enzymatic perfusion of the liver", Cell Biol. Int. Rep. 6:625–628. Briefly, the method of Guguen-Guillouzo et al. involves (i) isolating a liver or a portion thereof from which hepatocytes are to be harvested; (ii) introducing a cannula into the portal vein or a portal branch; (iii) perfusing the liver tissue, via the canula, with a calcium-free buffer followed by an enzymatic solution containing 0.025% collagenase (e.g., Type 4, from Sigma Chemical Company) in 0.075% calcium chloride solution in HEPES buffer at a flow rate of between 30 and 70 milliliters per minute at 37° C.; then (iv) mincing the perfused liver tissue into small (e.g. about 1 cubic millimeter) pieces; (v) continuing the enzymatic digestion in the same buffer as used in step (iii) for about 10–20 minutes with gentle stirring at 37° C. to produce a cell suspension; and (iv) collecting the released hepatocytes by filtering the cell suspension produced in step (v) through a 60–80 micrometer nylon mesh. The collected hepatocytes may then be washed three times in cold HEPES buffer at pH 7.0 using slow centrifugation (e.g., 50×g for five minutes) to remove collagenase and cell debris. Non-parenchymal cells may be removed by metrizamide gradient centrifugation. If the amount of liver tissue is too small to perform the above perfusion procedure, for example, less than 100 g of tissue, then the tissue may be minced and digested with collagenase solution with gentle stirring and processed according to steps (iv) and (v) of this paragraph.

It may be desirable to separate human hepatocytes prepared as set forth above into a subset for introduction into animals and another subset which is undesirable to propagate. For example, if a human subject is to serve as a donor for hepatocytes which are to be propagated in a chimeric animal according to the invention and then reintroduced into the subject, e.g., to reconstitute a liver damaged by infectious disease or malignancy, it would be desirable not to propagate hepatocytes which are infected or which have undergone malignant transformation. In such a situation, it would be desirable to eliminate infected or malignant hepatocytes from the population of hepatocytes which is to be introduced into the host animal. Elimination of unwanted cells can be performed by standard cell sorting techniques, for example fluorescence activated cell sorting using an antibody specific for the infectious agent or for malignant transformation. Alternatively, undesirable cells may be eliminated or attenuated by treatment with antiviral or antimicrobial compounds, radiation, antibody-ligated toxins, culture techniques, etc.

5.1.4. FAVORING PROLIFERATION OF HUMAN HEPATOCYTES

In particular non-limiting embodiments of the invention, selection pressure may be used to favor the proliferation of human hepatocytes. Such selection pressure is defined herein as including any condition, preexisting in the host animal at the time of introduction of donor cells or imposed thereafter, which results in a greater likelihood that human hepatocytes, rather than host hepatocytes, will proliferate.

For example, the selection pressure may result from the presence of a transgene that decreases the viability of host hepatocytes, either intrinsically (directly) or by administration of an activating agent (indirectly). Alternatively, human donor hepatocytes can be transfected with a protective gene that will enable those cells to survive subsequent exposure to a hepatotoxin. In one specific non-limiting example, the transgene may be the albumin promoter/urokinase construct, whereby as the host animal matures and the albumin promoter becomes active, host hepatocytes may be eliminated by the toxic effects of urokinase. In such cases, the selection pressure is maturation of the animal with consequent transgene activation. In a second specific non-limiting example, the transgene may be the albumin promoter/HSV-TK construct, whereby when gancyclovir is administered to the host animal (e.g., as an intraperitoneal injection of 250 mg/kg gancyclovir in sterile PBS), hepatocytes of the transgenic host may be selectively killed. In such embodiments, the death of host hepatocytes would be expected to favor compensatory proliferation of human hepatocytes. This can occur because of the known property of parenchymal liver cells to proliferate during conditions that stimulate regeneration.

It may be preferable to effect stepwise attenuation of host hepatocytes rather than eliminate a majority in a short period of time, as the sudden loss of liver function could result in death of the animal and/or conditions that would disfavor the establishment of a human hepatocyte population in the host liver. For example, administration of several doses of gancyclovir to a host animal transgenic for the albumin promoter/HSV-TK construct, beginning before and continuing after introduction of donor cells, may result in a gradual elimination of host cells, thereby permitting human hepatocytes to establish a "foothold" before the majority of host hepatocyte function is eliminated.

In another non-limiting embodiment, donor hepatocytes can be transfected with a protective gene. For example, a gene encoding an antisense RNA or ribozyme against the cytochromes 2E1, 1A2, and/or 3A4 (CYP2E1, CYP1A2, CYP3A4, respectively), would prevent activation of the drug acetaminophen. Metabolites of that agent within liver cells results in hepatocyte death. Thus, donor cells containing the transgene would have a survival advantage relative to host cells if massive doses of acetaminophen were administered after cell transplantation. A similar strategy would be to transfect a mutant RNA polymerase II that is resistant to the effects of the hepatotoxin phalloidin. Administration of phalloidin to hosts bearing transfected human hepatocytes producing the mutant polymerase would be protected and have a selective advantage over host cells.

5.1.5. CONFIRMING THE PRESENCE OF HUMAN HEPATOCYTES

The presence of human hepatocytes in a host may be evaluated by assaying for specific human markers. The presence of such markers in a blood sample or a liver biopsy collected from the animal (e.g., percutaneously) may be evaluated without affecting the viability of the animal. Alternatively, the success of chimerization may be evaluated retrospectively at necropsy.

As a specific example, the presence or absence of immunologically distinct human albumin may be determined in a blood or tissue sample by Western blot analysis or immunohistochemistry using antibody specific for human, but not host, albumin (see, for example, Wu et al., 1991, J. Biol. Chem. 266:14338–14342; Osborn and Weber, 1982, Meth. Cell Biol. 24:97–132). An example of a publicly available antibody specific for human albumin is Sigma #A6684 monoclonal anti-human albumin HSA II.

5.2. TOXICOLOGY MODEL SYSTEMS

In particular non-limiting embodiments of the invention, a chimeric animal prepared as set forth above may be used as a model system for human hepatocyte function in a toxicology study to determine the toxic effect(s) of a test agent on (i) the human hepatocytes present in the animal and/or (ii) the host animal itself. The chimeric animals of the invention provide the opportunity to recapitulate, in a model system, metabolism of the test agent by human hepatocytes, which may result in one or more secondary compounds that may not be produced when the test agent is exposed to non-human hepatocytes.

Because a test agent may have different effects on host hepatocytes and human hepatocytes, it is desirable to determine the relative proportion of human and host hepatocytes in each test animal, for example by quantitation of the amounts of human and non-human albumin in a serum sample. The ability of this measurement to accurately reflect liver cell populations may be established by correlating serum levels with hepatocyte populations as evaluated by immunohistochemistry in liver tissue samples obtained by biopsy or at necropsy. Once the relative proportions of hepatocyte populations for each animal are determined, experimental results relating to the effect of test agent may be compared with the effect of test agent on a control non-chimeric animal which represents a population of 100 percent host hepatocytes. Preferably, the host hepatocytes are less sensitive to test agent than human hepatocytes.

Accordingly, chimeric animals of the invention may be used to evaluate the toxic effect(s) of a test agent on the viability (survival, function) of human hepatocytes in the animal and/or the animal as a whole by subjecting at least one and preferably a plurality of chimeric animals and non-chimeric animals of the same species (as controls) to incremental doses of test agent. At one or a series of time point(s), the animal(s) may be evaluated by standard laboratory tests to determine whether toxic effects have occurred. Such an evaluation may include an assessment of bodily functions, as reflected by weight and/or activity and analysis of blood and/or urine, for example for test agent or its metabolites, markers of liver function and/or hepatocyte viability, kidney function, immune function, etc. As discussed above, such information is considered in view of the percentage of human hepatocytes in each test animal's liver and the relative effects of test agent on human versus host hepatocytes. Further, the percentage of human hepatocytes may change during the course of an experiment, for example, if the test agent is selectively toxic to human hepatocytes so that compensatory proliferation of host hepatocytes occurs. Accordingly, it is desirable to perform measurements of relative quantities of one or more marker specific for human hepatocytes at each time point; for example, the relative amounts of human and host albumin in serum may be measured by Western blot. At one or more time point of the study, an animal(s) may be biopsied and analyzed for human versus host albumin gene or gene product, or human-specific Alu repeat sequence, or sacrificed and a complete necropsy analysis be performed, including immunohistochemical evaluation of hepatocyte populations in the liver.

5.3. MODEL SYSTEMS FOR LIVER DISEASES

In another non-limiting embodiment of the invention, an animal having a chimeric liver may be used as a model system for human liver disease. Such chimeric animals may be used to create models of liver disease resulting from exposure to a toxin, infectious disease or malignancy. The model systems of the invention may be used to gain a better understanding of these diseases and also to identify agents which may prevent, retard or reverse the disease processes.

Where the chimeric animal is to be used as a model for liver disease caused by a toxin, animals prepared as set forth above may be allowed to mature to a point where the size of the human hepatocyte population is substantial (e.g. has approached a maximum), and then be exposed to a toxic agent. The amount of toxic agent required to produce results most closely mimicking the corresponding human condition may be determined by using a number of chimeric animals exposed to incremental doses of toxic agent. Examples of toxic agents include but are not limited to alcohol, acetaminophen, phenytoin, methyldopa, isoniazid, carbon tetrachloride, yellow phosphorous, and phalloidin.

In embodiments where a chimeric animal is to be used as a model for malignant liver disease, the malignancy may be produced by exposure to a transforming agent or by the introduction of malignant cells. The transforming agent or malignant cells may be introduced with the initial colonizing introduction of human hepatocytes or, preferably, after the human hepatocytes have begun to proliferate in the host animal. In the case of a transforming agent, it may be preferable to administer the agent at a time when human hepatocytes are actively proliferating. Examples of transforming agents include aflatoxin, dimethylnitrosamine, and a choline-deficient diet containing 0.05–0.1% w/w DL-ethionine (Farber and Sarma, 1987, in *Concepts and Theories in Carcinogenesis*, Maskens et al., eds, Elsevier, Amsterdam, pp. 185–220). Such transforming agents may be administered either systemically to the animal or locally into the liver itself. Malignant cells may preferably be inoculated directly into the liver.

Where the chimeric animal is to be used as a model for infectious liver disease, the infectious agent, or an appropriate portion thereof (e.g. a nucleic acid fragment) may be introduced with the initial introduction of hepatocytes or after the human hepatocytes have begun to proliferate. The infectious agent may be administered as a free entity or incorporated into a human cell such as a human liver cell. Examples of infectious diseases suitable for modeling include but are not limited to hepatitis A, hepatitis B, hepatitis C, hepatitis D, hepatitis E, malaria, Epstein Barr infection, cytomegalovirus infection. and Yellow Fever. For such models, it may be advantageous that the host animal has an immune system that is intact (but for the induced tolerance to the host cells), in that the animal's immune response to the infectious agent and/or infected human hepatocytes may produce a more accurate model of human liver diseases in which the immune system plays a pathogenic role. As such, it may be desirable to ensure that the cells/cell lysate used for tolerization not include infectious agent or related antigens. A working example in which the invention is used to produce a hepatitis B virus model system is set forth below.

Further, where the infectious agent is a virus, the present invention provides for chimeric animals comprising human hepatocytes that contain a nucleic acid of the virus, such as the entire viral genome or a portion thereof, or a nucleic acid encoded by the viral genome or a portion thereof.

5.3.1. HCV MODEL PRODUCED BY INFECTIOUS SERUM

In a particular non-limiting embodiment, the invention provides for a chimeric animal model for hepatitis C virus infection. Preferably, the chimeric animal is a mouse transgenic for a gene whose product is selectively toxic to hepatocytes, such as the albumin promoter/urokinase gene or the albumin promoter/HSV-TK gene. Hepatitis C infection of human hepatocytes in such mice may be produced either (i) concurrently with or preferably (ii) after the colonizing introduction of human hepatocytes and after the effects of the toxic transgene have attenuated or eliminated host hepatocytes. Preferably, the chimeric animal has, prior to infection, a liver which comprises substantially (at least about 20 percent, preferably at least 50 percent, more preferably at least 80 percent) human hepatocytes.

The source of infectious agent may be serum from one or more human subject infected with HCV but not demonstrably infected with one or more other agents that infect hepatocytes. Serum samples of genotype Ia may be assayed for viral load by branched DNA (bDNA) assay (Chiron, San Francisco, Calif.). Sera from non-infected subjects and individuals with non-viral hepatitis may be used to pseudo-infect control chimeric animals. Using standard biohazard precautions, serum containing HCV RNA in infectious human serum, at a titer ranging between about $10^3$–$10^7$ particles per milliliter may be injected intravenously into a chimeric transgenic mouse about 2–4 months and preferably about 6 weeks after colonization with human hepatocytes. Preferably, increasing amounts of HCV RNA in infectious human serum, with the viral titer previously determined (e.g., by National Genetics Institute, Los Angeles, Calif.) may be injected into a panel of such chimeric transgenic mice. The site of injection may be the tail vein, and the volume of serum injected may be 0.1–0.5 ml. The serum may preferably be filter sterilized prior to administration.

Serum may be collected from the chimeric mouse (mice) and tested to establish baseline and post-infection levels of liver function markers such as AST (aspartate amino transferase), ALT (alanine aminotransferase) and alkaline phosphatase. For example, baseline and weekly post-infection levels of AST, ALT and alkaline phosphatase in mouse sera may be determined spectrophotometrically using kits from Sigma Chemical Co., St. Louis, Mo., where appropriate standards are used to generate reference curves. Blood samples may be obtained from the animals retroorbitally using standard techniques.

The mouse (mice) may be tested for seroconversion against HCV by testing for circulating antibody (e.g., anti-C100-3 antibody), for example using the ELISA kit available from Ortho Diagnostics (catalog number 930740: Ortho HCV ver. 3.1 ELISA TEST SYSTEM; Ortho Diagnostics, Raritan, N.J.). Tests for seroconversion may be performed, for example, at weekly intervals for the first month after infection and then monthly.

Viral load may be determined (e.g., weekly) by assay of dilutions of serum for positive strand HCV RNA using thermostable rTth RT-PCR performed under stringent conditions (at 70° C.) to eliminate false priming of the incorrect strand. Branched DNA analysis may also be used, but it is not as sensitive. For positive strand RNA analysis, the cDNA reverse primer may be: 5'-TCGCGACCCA ACACTACTC 3' (SEQ ID NO: 2) and the forward primer may be 5'-GGGGGCGACA CTCCACCA-3' (SEQ ID NO: 3). PCR amplification in the absence of reverse transcriptase activity may be accomplished by chelating manganese and magnesium ions as described in (Lanford et al., 1995, J. Virol. 69:8079–8083). The amplified product, which spans nucleotides 15–274 of the 5'-NTR of HCV may be quantitated by Southern blotting using a detectably labeled probe against a region internal to the primers.

Liver tissue obtained by biopsy or from a sacrificed animal may be evaluated for HCV replication and for histopathological changes. Biopsy may be performed by anesthetizing the chimeric mouse with intramuscular injections of ketamine (40 mg/kg) and xylazine (5 mg/kg), cleaning the abdominal area with alcohol and betadine wipes, making a 1 cm incision in the abdominal wall to expose the liver, and collecting a sliver (approximately 10 mg) of liver tissue. Afterward, 100U of sterile thrombin may be administered locally at the biopsy site followed by application of gel foam to inhibit bleeding, the abdominal wall may be closed with dissolvable sutures, and the skin may be closed with nylon sutures. Viral replication may be quantitated by measuring the amount of negative strand template HCV RNA in liver RNA (prepared, for example, as set forth in Chomczynski and Sacchi, 1987, Anal. Biochem. 162:156–159), using rTth RT-PCR (Lanford et al., 1995, J. Virol. 69:8079–8083). To assess liver histology, liver tissue may be fixed and sectioned and stained with hematoxylin-eosin or trichrome to evaluate, respectively, inflammation or fibrosis. A standardized scoring method, such as Knodell scoring (Knodell et al., 1981, Hepatology 1:531), may be used. The presence or absence of neoplastic lesions may be evaluated.

To determine the optimum conditions for producing an HCV infected chimeric animal, the time course of serum aminotransferases AST and ALT, alkaline phosphatase levels, and viral RNA loads may be plotted as a function of time and the minimum number of viral equivalents required to sustain an infection determined. Levels of detectable HCV RNA in the serum of an animal may be used as an indicator of the chronicity of infection.

Potential problems associated with the foregoing embodiment are as follows. First, the detection of negative strand HCV template as a measure of HCV replication may be problematic due to the requirement for amplification techniques and the possibility of inadvertent amplification of positive strand. The method of Lanford et al. (supra) using stringent conditions for priming of the RT-PCR and inactivation of the reverse transcriptase by chelation prior to PCR of the cDNA has been shown to reduce false amplification to $1/10^4$–$1/10^5$. Second, the fact that mouse hepatitis virus may be found even in "pathogen free" environments makes it desirable to confirm that host animals are free of the virus, for example using a mouse virus screen as available from Microbiological Associates, Inc., Rockville, Md. (Carlson et al., 1989, J. Clin. Invest. 83:1183–1190), where animals testing positive are not used as hosts. Third, infection may be improved by increasing the amount of human serum used in the inoculum.

The foregoing description may be applied to nontransgenic mice or other animals and may be adapted, by altering volume of inoculum and time between colonization and inoculation proportionately, to larger animal model systems.

5.3.2. HCV MODEL PRODUCED BY INFECTIOUS PLASMID

In a related embodiment, infection may be introduced by HCV plasmid (Kolykhalov et al., 1997, Science 277:570–574) complexed to a liver-specific protein carrier, such as AsOR-PL or AsORlysine-VSVG, where AsOR-PL is asialoorosomucoid polylysine and AsORlysine-VSVG is asialoorosomucoid covalently linked to L-lysine methyl ester and a synthetic 25 amino acid peptide of the VSVG protein. The DNA-protein complex may be formed by slowly adding protein conjugate in 25 microliter aliquots to DNA in 0.15M NaCl with continuous vortexing at room temperature. After 30 minutes of incubation at room temperature absorption at 260 nm, 340 nm and 400 nm may be measured to detect complex formation. Complexes may be filter sterilized by passage through a 0.22 micron filter. About 10 micrograms of the DNA/protein complex in 0.5 milliliters sterile saline may then be injected into the tail vein of a mouse.

5.3.3. HCV MODEL PRODUCED BY TRANSPLANTING INFECTED HEPATOCYTES

As an alternative to producing HCV infection by inoculation with infected serum, infection may be produced by transplanting HCV infected hepatocytes into a chimeric animal. Although the infected hepatocytes may be introduced during colonization with human cells, it is preferred that they be introduced into chimeric livers having a substantial population of human hepatocytes. Preferably, the chimeric animal is a mouse transgenic for a gene whose product is selectively toxic to hepatocytes, such as the albumin promoter/urokinase gene or the albumin promoter/HSV-TK gene.

Infected human hepatocytes may be obtained as described in Lieber et al., 1996, J. Virol. 70:8782–8791. Using appropriate pathogen-containment procedures, human liver specimens may be obtained from HCV-infected liver transplant recipients. An apical piece of liver covered on three sides by capsule may be perfused with buffer without calcium and then with collagenase in perfusion buffer with calcium. Hepatocytes may then be pelleted by low speed centrifugation. Non-parenchymal cells may be separated from parenchymal hepatocytes by metrizamide gradient centrifugation. The viability of isolated hepatocytes may be evaluated by trypan blue exclusion. Hepatocytes may be resuspended in Williams medium at about $10^7$ cells per milliliter.

The infected hepatocytes may then be introduced into the liver of a chimeric animal such as a chimeric transgenic mouse having a liver which comprises substantially (at least about 20 percent, preferably at least 50 percent, more preferably at least 80 percent) human hepatocytes. The infected hepatocytes may be introduced by intrasplenic injection. Where the animal is a mouse, hepatocytes may be achieved by anesthetizing the animal with ketamine (90 mg/kg)/xylazine (10 mg/kg), and then, under aseptic conditions, making a 2–3 millimeter incision in the left paracostal area, exposing the spleen. The spleen may then be exteriorized and infected hepatocytes may be injected slowly into the spleen parenchyma. Gel foam may be used to achieve hemostasis, the spleen may be restored into the body cavity, and the wound may be sutured closed. Monitoring of the resulting infected animals for serconversion, viral load, serum levels of protein markers of liver function, and histopathology may be performed as described in section 5.3.1. Further, these methods may be applied to nontransgenic mice and may be adapted for use in larger animals.

5.3.4. USE OF HCV MODELS

Chimeric animal models of HCV infection may be used not only to study the biology of HCV, but also to identify agents that may prevent or inhibit HCV infection and/or replication. For example, to determine whether a test agent inhibits infection by HCV, the effect of the agent on preventing infection when administered prior to or contemporaneously with injection of infected serum may be evaluated. Similarly, the effect of a test agent administered during the course of infection may be assessed. Parameters useful in determining the effectiveness of test agent would include whether and when the test animal seroconverts with respect to HCV, the viral load, the ability of serum from the animal to infect other animals, blood levels of proteins/enzymes associated with liver function and/or hepatocyte viability, and liver histology.

5.4. CHIMERIC ANIMALS AS A SOURCE OF HEPATOCYTES FOR LIVER RECONSTITUTION

The present invention further provides for the use of chimeric animals as a source of human hepatocytes for liver reconstitution in a second host subject. Such reconstitution may be used, for example, to (i) produce a "next generation" chimeric non-human animal; (ii) introduce genetically modified hepatocytes for "gene therapy" of the second host subject; or (iii) replace hepatocytes lost as a result of disease, physical or chemical injury, or malignancy in the second host. Human hepatocytes collected from a chimeric animal are said to be "passaged".

For any of these applications, liver tissue from a chimeric animal may be used to produce a cell suspension and then human hepatocytes may be separated from non-human hepatocytes and other cells. The liver tissue may be processed as set forth above to produce a suspension of hepatocytes. As a non-limiting specific example, where the chimeric animal is a mouse or rat, hepatocytes may be prepared by the following method, adapted from Seglen, 1976, "Preparation of rat liver cells", Methods Cell Biol. 13:29. Briefly, a chimeric mouse or rat may be anesthetized with ketamine/xylazine, its abdomen may be shaved and decontaminated, the peritoneal cavity may be opened by incision, the inferior vena cava may be cannulated, the portal vein may be divided and the suprahepatic vena cava may be ligated. Then, the liver may be perfused in situ with calcium free balanced salt solution at 5 ml/min for five minutes at 37° C., followed by perfusion with 0.05% collagenase (e.g., type IV, from Sigma Chemical Co.) in 1% albumin and balanced salt solution for 20 minutes. The liver may then be transferred to a Petri dish, and minced to produce a cell suspension, from which hepatocytes may be collected by passage through a 60–80 micron nylon mesh. The collected cells may then be washed three times in RPMI 1640 or Williams E medium with 10% fetal bovine serum, and then centrifuged at 35×g for five minutes at 4° C. Hepatocytes may be purified through a metrizamide gradient and resuspended in RPMI 1640 or Williams E medium.

Human hepatocytes may be separated from non-human cells using fluorescence activated cell sorting techniques and an antibody which selectively binds to human hepatocytes, for example but not by way of limitation, an antibody that specifically binds to a class I major histocompatibility antigen. Suitable antibodies would include but not be limited to anti-human HLA-A, B, C, Pharmingen catalogue #32294X or #32295X, FITC mouse κb, PharMingen catologue #06104D (PharMingen, San Diego, Calif.) See, for example, the procedure described in Markus et al., 1997, Cell Transplantation 6:455–462.

Human hepatocytes may be passaged through cell transplantation of tolerized host animals, using the techniques set forth above. In this manner, cells obtained from an initial human donor may be utilized in a multitude of chimeric animals and over an extended period of time, potentially reducing the variability that may be encountered in chimeric animals produced using hepatocytes obtained from diverse hosts.

Passaged human hepatocytes may also be used for gene therapy applications. In the broadest sense, such hepatocytes are transplanted into a human host to correct a genetic defect. The passaged hepatocytes need not, but are preferably derived originally from the same individual who is to be the recipient of the transplant. However, according to the invention, hepatocytes from a different individual may alternatively be used.

As a specific, non-limiting example, a patient suffering from intermittent acute porphyria, caused by a genetic defect in the expression of uroporphyrinogen I synthase, may benefit from transplantation of human hepatocytes harvested from a chimeric animal of the invention, where the transplanted cells are genetically normal in their expression of that enzyme. The recipient would be "matched" for transplantation antigens with the original donor, or be treated with immunosuppressive therapy. For such applications, chimeric animals prepared from a wide diversity of individual donors could provide the advantage of constituting a "living library" of differentiated hepatocytes having various transplantation antigen profiles, thereby obviating the need for waiting until liver tissue from a genetically suitable donor becomes available.

Preferably, however, the original donor and eventual recipient of passaged hepatocytes are the same person, thereby eliminating the need for immunosuppression. For gene therapy applications, (i) hepatocytes may be harvested from the subject, (ii) the desired genetic construct may be introduced into those hepatocytes, (iii) the resulting genetically engineered human hepatocytes may be used to tolerize a host animal to their presence, (iv) construct-carrying hepatocytes may be introduced into the tolerized animal such that its liver is colonized, and then, once expanded in number, (v) the transgenic hepatocytes may be harvested from the chimeric animal and (vi) reintroduced into the subject. A genetic construct may be introduced into the human hepatocytes by any standard method, including, but not limited to, transfection with naked DNA, microparticles or liposomes, or infection with a viral vector, such as an adenoviral vector, an adeno-associated vector, or a retroviral vector. Hepatocytes used for colonization may be enriched for cells containing the desired construct, for example, by selection by culture conditions, antibody/FACS methods, etc. which eliminate cells lacking the construct.

Alternatively, the hepatocytes may be used to colonize the liver of a tolerized animal prior to or contemporaneous with the introduction of the desired transgene via a gene therapy vector. This approach may be more problematic because the host animal could develop an immune response directed toward either the vector or vector-transformed hepatocytes.

In further embodiments, human hepatocytes passaged through a chimeric animal of the invention may be used to reconstitute liver tissue in a subject as a prelude or an alternative to liver transplant. As a specific non-limiting example, a subject suffering from progressive degeneration of the liver, for example, as a result of alcoholism, may serve as a donor of hepatocytes which are then maintained, through one or several generations, in one or more chimeric animal. As a result of maintenance in such animal(s), the number of hepatocytes is expanded relative to the number originally harvested from the subject (it may be preferable to use larger animals to produce greater numbers of cells). At some later date, when the subject's liver has deteriorated to a medically hazardous condition, hepatocytes passaged in the chimeric animal(s) may be used to reconstitute the subject's liver function. As a second non-limiting example, passaging hepatocytes may be used not only to expand the number of hepatocytes but also to selectively remove hepatocytes that are afflicted with infectious or malignant disease. Specifically, a subject may be suffering from hepatitis, where some but not all of the hepatocytes are infected and infected hepatocytes can be identified by the presence of viral antigens on the cell surface. In such an instance, hepatocytes may be collected from the subject, and non-infected cells may be selected for passaging in one or more chimeric animal, for example by FACS. Meanwhile, aggressive steps could be taken to eliminate infection in the patient. Afterward, the subjects liver tissue may be reconstituted by hepatocytes passaged in a chimeric animal. An analogous method could be used to selectively passage non-malignant cells from a patient suffering from a primary or secondary (e.g. metastatic) liver malignancy. Thus, the chimeric animals of the invention may be used as a means of purging unwanted hepatocytes from a human subject.

6. EXAMPLE: PREPARATION OF RATS HAVING CHIMERIC LIVERS

6.1. SURVIVAL OF HUMAN HEPATOCYTES IN RATS TOLERIZED BY INTRAPERITONEAL INJECTION

To tolerize hosts for hepatocyte transplantation, human hepatocytes obtained from Clonetics Corp. were suspended at a concentration of $10^6$ cells/ml saline and sonicated. Laparotomies were performed to expose the gravid uteri of pregnant rats and sterile filtered sonicates equivalent to $10^4$ hepatocytes in 10 µl were injected into groups of three fetuses each. A control received only the same volume of normal saline. Within 24 hrs of birth, transplantation of hepatocytes were performed by the method of Marucci et al., 1997, Hepatol. 26: 1195–1202. An incision was made at the left paracostal area, the spleen was visualized and $2\times10^7$ hepatocytes in 100 µl sterile medium were injected slowly into the spleen. To evaluate the status of immune tolerance, two experiments were performed: a) mixed lymphocyte assays and b) repeat transplantation challenges.

6.1.1. MIXED LYMPHOCYTE ASSAYS

For mixed lymphocyte assays, spleens from intrafetally injected animals were removed six weeks after birth, and spleen cells were isolated as described by Henry and Watson (1980, "Preparation of Spleen Cells" section 2.9, in *Selected Methods in Cellular Immunology*, Mishell and Shiigi, eds., WH Freeman and Co., p.65). Assays were performed according to the method of Bradley (1980, "Mixed Lymphocyte Responses" section 6.3, in *Selected Methods in Cellular Immunology*, Mishell and Shiigi, eds., WH Freeman and Co., p. 162) in which spleen cells were used as responder cells and human hepatocytes (identical to those transplanted but treated with 2000R of X-irradiation to prevent proliferation) were used as stimulator cells. Human hepatocytes should not stimulate lymphocyte proliferation in spleen cells from immunotolerant animals, but should in cells from non-tolerant animals.

Spleen cells, $7\times10^5$ cells per assay, from fetuses previously injected intraperitoneally as described above with hepatocyte lysates alone, lysates followed by hepatocytes after birth, or controls were mixed with $3\times10^5$ X-irradiated simulator hepatocytes. Controls consisted of spleen cells from saline treated fetuses alone, and those same cells plus irradiated spleen cells from non-treated animals. Cells were pulsed with 1 $\mu C^3$[H]-thymidine (specific activity 5 Ci/mmole) at 37° C. for 72 hours, and then harvested by TCA precipitation onto Whatman glass fiber filters, washed and scintillation counted. All assays were performed in quadruplicate, and the entire experiment done in duplicate. The results are expressed as means±S.D. in units of cpm/$10^6$ responder cells in FIG. 1.

FIG. 1 shows that spleen cells from animals that did not receive hepatocyte lysate when they were fetuses incorporated approximately 5,200 cpm/$10^6$ cells when stimulated with irradiated human hepatocytes. In contrast, stimulation of spleen cells derived from animals that did receive human hepatocyte lysate when they were fetuses was significantly less (less than 1000 cpm/$10^6$ cells [p<0.002]) than that observed using cells from animals that did not receive lysate. In fact, cells derived from animals injected with lysates resulted in stimulation that was no more than background levels of spleen cells alone. Irradiated hepatocytes alone (without spleen responder cells) had no significant radioactive incorporation confirming that the irradiation substantially blocked any contribution to the observed radioactive uptake.

These data indicate that spleen cells removed 6 weeks after birth from rats previously injected as fetuses with human hepatocyte lysates are not significantly stimulated to proliferate by the presence of human hepatocytes. At this time point, human albumin is still strongly detectable in serum in the tolerized animals. Together, the data indicate that immune tolerance to human hepatocytes was achieved.

6.1.2. RECHALLENGE WITH ADDITIONAL HEPATOCYTE TRANSPLANTATIONS

As further evidence for immune tolerization, groups of rats previously tolerized and transplanted as described above were subjected to a repeat transplantation. If the rats were not rendered immunologically tolerant to human hepatocytes, a second transplantation of human cells would be expected to evoke an anamnestic response and rapid rejection of those cells. To evaluate that possibility, rats tolerized intrafetally and transplanted with human hepatocytes at birth as described above were given a repeat transplantation of $2\times10^6$ cells 6 weeks after the first. Serum was assayed for human serum albumin using a specific anti-human albumin antibody and analyzed by Western blots as shown in FIG. 2.

In FIG. 2, lane 1 contains 40 ng of human serum albumin standard, and lane 2 shows that there was human albumin still present in substantial concentration in serum at 6 weeks after an initial cell transplantation. After a second injection of human cells the amount of serum albumin increased 24 hrs later (lane 3), and continued to rise at least 8 days after the repeat dose of cells (lane 4). Animals that had not been tolerized (received only a fetal injection of saline) had no detectable human serum albumin even after a repeat transplant of human hepatocytes under identical conditions and assayed at the same time point (8 days; lane 5). These data suggest that human hepatocytes did not survive in non-tolerized animals. In contrast, in those animals that were tolerized, human hepatocytes not only survived each of two successive inoculations, but also maintained function as evidenced by serum albumin production.

6.1.3. SURVIVAL OF HUMAN HEPATOCYTES

Seventeen day old normal Sprague-Dawley rat fetuses were given lysates of $0.5 \times 10^5$ human hepatocytes by intrauterine inoculation into the peritoneum under transillumination. Following birth, $2 \times 10^5$ normal human hepatocytes were injected into the spleen. This is known to result in near total migration of transplanted hepatocytes to the liver (Attavar, et al., 1997, Hepatol. 26: 1287–1295). At weekly intervals, animals were bled via their tail veins and human serum albumin was detected as a function of time by Western blot analysis using a specific affinity purified rabbit anti-human albumin antibody (FIG. 3). At the conclusion of the study, animals were sacrificed and liver slices stained with anti-human albumin antibody and developed with a Texas red secondary antibody. Cells were visualized using a Zeiss confocal scanning microscope, model CLSM4 10 and images were captured as shown in FIG. 4.

FIG. 3 shows a representative Western blot of the collected rat sera, where lane 1 contains 10 ng standard human serum albumin, lane 2 contains 10 ng standard rat albumin, lane 3 contains rat serum I week after intrasplenic injection into the tolerized rat (1 day after birth), lane 4 contains serum from the same rat as lane 3 but after 2 weeks, lane 5 same as lane 3, but after 3 weeks. Lane 1 shows that the anti-human albumin antibody reacted with standard human serum albumin, but not with rat albumin, (lane 2) (nor mouse albumin, data not shown). Lanes 3, 4, and 5 showed bands corresponding in mobility to albumin detectable at about 10 ng/50 $\mu$g total serum protein. This level remained stable or increased through at least week 3. Transplantation of human IMR-90 fibroblasts under identical conditions failed to produce any detectable human serum albumin.

FIGS. 4A–D shows a representative immunofluorescence study of a liver section taken from 1 of 4 rats 3 weeks after injection with human hepatocyte lysate in utero, followed by intrasplenic injection of human hepatocytes. Immunocytochemistry was performed with primary antibody for human albumin, or rat albumin as a control, and Texas red-coupled secondary antibody. Panel A shows anti-human albumin antibody staining of rat liver without human hepatocyte transplantation. Panel B shows rat livers 3 weeks following injection with human hepatocyte lysate in utero and intrasplenic injection of human hepatocytes (1 day after birth) stained with anti-human albumin antibody and Texas Red second antibody. Panel C shows the same section as depicted in B, but without second antibody. Panel D shows a section of control rat liver after only intrauterine injection of human hepatocyte lysate developed with anti-human albumin antibody and Texas Red second antibody. Anti-human albumin staining of liver transplanted with human hepatocytes, but without prior injection with hepatocyte lysate was essentially the same as that shown in Panel A. There was no anti-human albumin staining of normal (non-transplanted rat liver) in Panel A. Cells with fluorescent cytoplasm are seen in Panel B, after both in utero lysate injection and human hepatocyte transplantation. This staining was not due to intrinsic fluorescence as there was no signal without second antibody as shown in Panel C. Finally, Panel D shows that the fluorescence could not be due to human albumin from the hepatocyte lysate alone. All 3 other animals injected with human hepatocyte lysate in utero and intrasplenic injection of human hepatocytes showed similar results.

FIG. 5 is a photomicrograph of the same section of rat liver as depicted in FIG. 4B, 3 weeks after intrasplenic injection of human hepatocytes, here stained with hematoxylin and eosin. The human hepatocytes cannot be distinguished from the rat cells, and there appears to be no inflammation or other evidence of rejection.

FIGS. 6A–D shows the results of an immunofluorescence study performed six weeks after cell transplantation in tolerized animals. Aggregates of cells staining positive for human albumin were present in a tolerized rat that had received a human hepatocyte transplant, panel A. The same section without second antibody, panel B; or no antibody at all failed to produce a fluorescent signal, panel C. Furthermore, a liver section from a non-tolerized animal that had received a human hepatocyte transplant also produced no stained cells after 6 weeks, panel D. Scanning many fields also showed that most of the positive cells at 6 weeks were in groups, while sections taken at 2 weeks showed scattered single cells, predominantly. Because the injected cell suspensions were predominantly single cells, and because the fluorescence data at 2 weeks showed predominantly isolated single cells, the finding of groups of cells at 6 weeks suggests that the human cells transplanted into tolerized rats not only survived, but proliferated to some extent in the host liver environment.

6.1.4. INDUCTION OF TOLERANCE TO HUMAN HEPATOCYTES BY INTRATHYMIC INJECTION IN NEONATAL RATS

Injection of human hepatocytes was performed according to the method of Fabrega et al., 1995, Transplantation 59:1362–1364. $10^2$ human hepatocytes in 5 $\mu$l sterile medium were injected into the thymuses of 1–2 hour old newborn rats. Five days following intrathymic injection, $10^5$ human hepatocytes in 200 $\mu$l sterile medium was injected into the spleen (Marucci et al., 1997, Hepatol. 26:1195–1202). Blood was collected by tail vein puncture at the time of intrathymic injection and at weekly intervals following intrasplenic injection of hepatocytes and assayed for human albumin by Western blot analysis.

A representative Western blot of serum from one of 6 animals after intrathymic tolerization, followed by transplantation of human hepatocytes, is shown in FIG. 7. Lane 1 contains 10 ng standard human albumin; lane 2 contains 10 ng standard rat albumin and lanes 3–7 contain sera taken at the indicated times after transplantation of human hepatocytes. The data show that human albumin production increased until about 5 weeks and then remained stable. The other five animals had shown similar results.

7. EXAMPLE: A MODEL FOR HEPATITIS B VIRUS INFECTION 7.1 PURIFICATION OF HBV PARTICLES FROM HEPG2 2.2.15 CELLS

To test the possibility of infection of human hepatocytes in vivo, infectious HBV particles were prepared from the HepG2 2.2.15 cell line (obtained from Dr. George Acs, Mt. Sinai School of Medicine, N.Y.) which contains an integrated tandem repeat genome of HBV ayw strain. The cell line actively secretes infectious virus into the medium (Sells et al., 1988, J. Virol 62:2836–2844). Culture medium from HepG2 2.2.15 was clarified by centrifugation at 5,000 rpm, 4° C. for 30 min. The supernatant was layered on a 5 ml 25% sucrose cushion in TEN buffer (150 mM NaCl, 20 mM Tris-HCl, pH 7.4) and centrifuged at 25,000 rpm for 16 hrs at 4° C. The resulting pellet was resuspended in TEN buffer, applied onto a 20–50% continuous CsCl gradient, and centrifuged at 35,000 rpm for 16 hrs at 4° C. Fractions with buoyant densities between 1.24 g/ml and 1.28 g/ml containing HBV virus were collected, dialyzed against TEN and sterile filtered through 0.22$\mu$ filters.

7.2 INFECTION OF HUMAN HEPATOCYTES TRANSPLANTED INTO TOLERIZED RAT HOSTS

To determine whether human hepatocytes in rat liver could be infected with human hepatitis virus, one week after human hepatocyte transplantations, tolerized rats were given intrasplenic injections of $10^4$ hepatitis B viral particles (purified from HepG2 2.2.15 cells as described above) in 50 µl. Control animals tolerized but without human hepatocyte transplants, and tolerized transplanted animals without HBV were used as controls. Liver sections were removed by liver biopsy at 1 week, and partial hepatectomy at 6 weeks and 14 weeks post HBV treatment and analyzed as described below.

7.3 IDENTIFICATION OF THE PRESENCE OF HUMAN LIVER CELLS AND HBV INFECTION

Figure 8A:
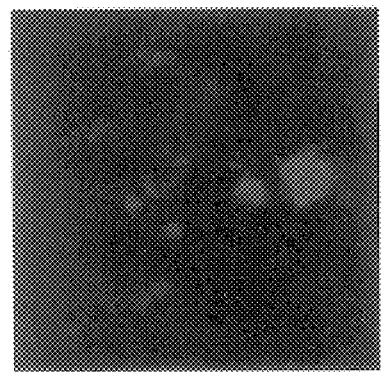
Figure 8B:
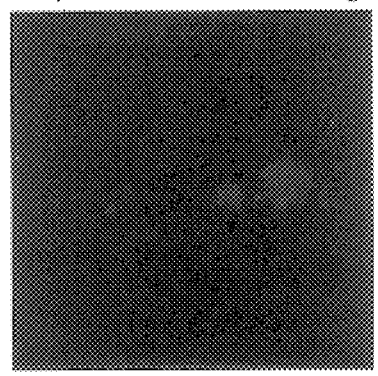
Figure 8C:
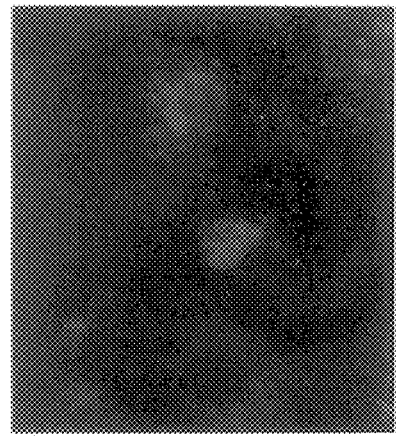
Figure 8D:
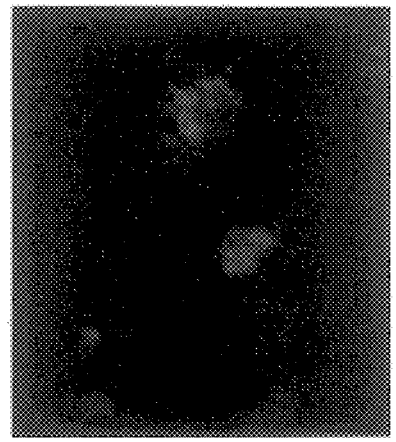
Figure 8E:
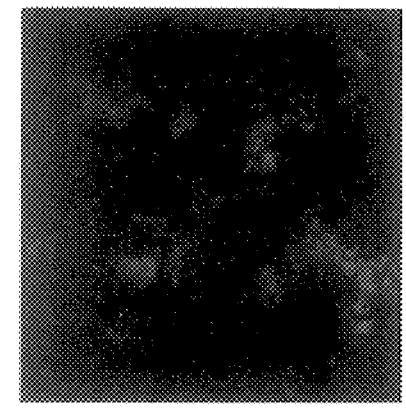
Figure 8F:
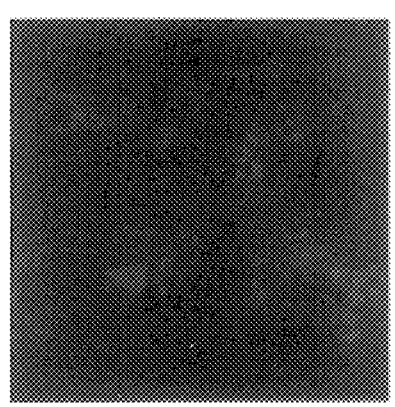

To identify and quantify human hepatocytes in host liver, immunohistochemical staining for human albumin was used. Visualization of cells infected with HBV was similarly achieved by immunohistochemical staining for Hepatitis B Surface Antigen (HBsAg). Liver tissues were flash frozen in liquid nitrogen immediately following removal. Samples were prepared according to the method of Osborne and Weber (1982, Meth. Cell Biol. 24:97–132) with minor modifications. Liver cryosections 6 µm thick were fixed in 4% paraformaldehyde for 15 min at 25° C., and washed 3 times with phosphate buffered saline (PBS) pH 7.2. Liver sections were quenched with 10% non-fat milk in PBS for 30 min at 25° C. followed by successive incubations with 1/1000 dilution of rabbit anti-human albumin (Sigma). Identical sections were stained with 1/1000 dilution of goat anti-HBV surface antigen (DAKKO). Each section was incubated for 2 hrs at room temperature. Between each primary antibody incubation, liver sections were exposed to 10% non-fat milk in PBS containing 0.05% NP-40 and 3 times with 10% non-fat milk in PBS alone. Texas red-conjugated anti-rabbit antibody (1/100 dilution) was used to develop anti-human albumin and FITC conjugated anti-goat (1/100 dilution) antibody was used to develop anti-HBsAg. Sections were incubated with the second antibodies for 30 min at 25° C. Following 3 washes with 10% non-fat milk in PBS, and a final PBS wash, sections were treated with anti-fade 2.5% 1/4-diazobicyclo-[2.2.2]-octane (DABCO) (Sigma), covered with cover slips and stored at 20° C. in light-proof boxes. Immunofluorescence of liver sections were visualized with Zeiss Scanning laser confocal microscope (Model LSM-410, Carl Zeiss, New York) using 63× objective. Frozen sections of chimeric liver were incubated with antibodies against human albumin and HBV surface antigen to detect the presence of human albumin and HBV proteins. Human albumin was detected with Texas red conjugated secondary antibody and HBV surface antigen detected with the use of FITC-conjugated second antibody. FIGS. 8A–F clearly demonstrates that both human albumin, left panels 8A, 8C and 8E, and HBV surface antigen, right FIGS. 8B, 8D, and 8F, were clearly detectable within cells in livers of tolerized rats transplanted with human hepatocytes followed by HBV treatment at 1 week (FIGS. 8A and 8B); 6 weeks (FIGS. 8C and 8D); and 14 weeks (FIGS. 8E and 8F). Furthermore, the staining for HBsAg appears to present only in cells that also stained for albumin. However, many cells that contained albumin were also positive for HBV. In a liver sample obtained 14 weeks after injection with HBV, FIGS. 9A–H shows that albumin stained cells were only found in animals that had been tolerized and had received transplanted human hepatocytes (FIGS. 9A and 9C). Animals without human cell transplants that received HBV had no albumin signal (FIG. 9E). Only tolerized animals that received human hepatocyte cell transplants prior to infection had HBsAg staining (FIG. 9B). As expected, the same animals without HBV infection failed to show any HBsAg staining indicating that the signal seen in FIG. 9B was not a non-specific artifact. Furthermore, animals that had no human cells, but did receive HBV injection also had no HBsAg signal (FIGS. 9E and 9F). The data indicate that injected virus had already been completely cleared by the time the liver sample was obtained and that the signal observed in row 1 was due to the infection of cells, and was not an artifact of circulating injected HBV. FIGS. 9G and 9H show that, in the same samples as depicted in FIGS. 9A and 9B, but without primary antibody, there was no signal corresponding to either albumin (FIG. 9G) or HBsAg (FIG. 9H), indicating the staining was not due to non-specific binding of second antibody to the tissue specimens.

7.4 HISTOLOGICAL EVALUATION OF LIVERS EXPOSED TO HBV

To determine whether exposure of human hepatocyte transplants to HBV could result in a histological hepatitis in vivo, serial slide sections were stained with hematoxylin and eosin and examined in a blinded fashion by a pathologist. The results, discussed below, are shown in FIGS. 13A–C and 14A–C.

7.5 ASSESSMENT OF FUNCTION OF TRANSPLANTED HUMAN HEPATOCYTES

Because albumin synthesis is a selective function of hepatocytes, levels of albumin mRNA were used to determine the activity of transplanted human cells in host liver. To accomplish this, specific primers for human and rat (control) albumin were used. HBV mRNA was detected similarly. Total RNA was extracted from 100 mg liver tissue with acid guanidinium thiocyanate according to the method of Chomczynski and Sacci (1987, Anal. Biochem. 162: 156–159). Poly A+ RNA was isolated from total RNA by the method of Aviv and Leder (1972, Proc. Natl. Acad. Sci. USA 69: 1408–1412). RNA was reverse transcribed and amplified by polymerase chain reaction according to the method of Berchtold (1989, Nucl. Acids Res. 17: 453) with some modifications. Briefly, 10 µg total RNA or 1 µg polyA+ RNA was mixed with 2 pmol of random primer (Gibco/BRL, Gaitherburg, Md.) at 70° C. for 15 min, and then cooled on ice. Two hundred units of Moloney Murine Leukemia Virus reverse transcriptase (Gibco/BRL, Gaithersburg, Md.) was used to reverse transcribe the RNA for 50 min at 42° C. Reaction was stopped by heating to 70° C. for 15 min, after which the cocktail was chilled on ice and treated with 10 µg RNase A at 37° C. for 20 min.

From the total cDNA, polymerase chain amplification of human albumin was performed using, as antisense primer, 5'-CCTTGGTGTTGATTGCCTTTGCTC-3' (SEQ ID NO: 4) and as sense primer, 5'-CATCACATCAACCTCTGTCTGACC-3' (SEQ ID NO: 5). If present, the albumin cDNA would generate a characteristic 315 bp fragment of the human albumin gene spanning nucleotides 176–491. For rat albumin, an antisense primer 5'-ATAGTGTCCCAGAAAGCTGGTAGGG-3' (SEQ ID No: 6) and a sense primer: 5'-CGGTTTAAGGACTTAGGAGAACAGC-3' (SEQ ID No: 7) were used to generate an expected 400 bp fragment of the rat albumin gene spanning nucleotides 104–504. To search for the presence of HBV in liver, an antisense primer 5'-ATCTTCTGCGACGCGGCGATGGAGATC-3' (SEQ ID No: 8) and a sense primer 5'-CTCTGCTGGGGGGAATTGATGACTCTAGC-3' (SEQ ID NO: 9) were used to generate a characteristic 355 bp fragment of the ayw HBV genome spanning nucleotides 2079–2434. One third of the total cDNA was mixed with 100 pmol of amplification primers and 2.5 U Taq polymerase and amplified at 1 cycle at 94° C. for 3 min, then for 38 cycles of 94° C. for 1 min, 55° C. for 1 min, and 72° C. for 1 min; and then 1 cycle at 72° for 5 min. The PCR products were analyzed on 1.0% agarose gels in Tris-Borate-Acetate buffer.

FIG. 10, lanes 1 and 2 show that the RT-PCR products of albumin from rat and human can be completely distinguished from each other based on electrophoretic mobility. Lane 4 shows RNA from HepG2 2.2.15 cells demonstrating a strong level of albumin synthesis in these cells. In tolerized animals that had human hepatocyte transplants, the rat albumin signal had the same intensity in cells infected with HBV (lanes 5 and 6) compared to those which were not (lanes 7 and 8). However, the human albumin mRNA signal in cells infected with HBV (lanes 5 and 6) appeared to be increased compared to non-infected cells (lanes 7 and 8). As expected, control animals that had no human hepatocyte transplants, but were administered HBV, had no detectable human albumin signal (lanes 9 and 10).

A time course of the levels of human albumin and HBV message is shown in FIG. 11. Compared to albumin RNA from human liver cells in the upper panel, lane 3, and from HepG2 2.2.15 cells lane 4, human albumin messenger RNA signal at 317 bp was easily detectable at one week after HBV infection, lane 5; with at least equal signal from week 6 and 14, lanes 6 and 7, respectively.

FIG. 11, bottom panel shows that HBV RNA could be detected in livers by the presence of a 355 bp band at 1 week after injection, lane 5. The intensity appeared to increase slightly at 6 weeks, lane 6; and remained strong at 14 weeks, lane 7, after HBV inoculation. The same primers were used to amplify HBV RNA from a human liver cell line HepG2 2.2.15 that continually produces HBV and was used as the source of HBV viral particles for the infections. FIG. 12 shows that HBV RNA could not be detected in livers of tolerized rats that did not receive hepatocyte transplantation, but received HBV (lanes 9, 10), indicating that the signal was not due to residual injected HBV.

FIGS. 13A–C depicts slides of livers from tolerized rats, transplanted with human hepatocytes and infected with HBV, at low power (20×). FIG. 13A shows that liver, one week after infection, has normal architecture for that stage in life and no evidence of inflammatory cell infiltration. However, after 6 weeks (FIG. 13B), foci of necrosis and mononuclear cell infiltrates can be seen. FIG. 13C shows substantial mononuclear inflammation after 14 weeks with an increase in Kupffer cells as well. FIGS. 14A–C shows that at high power (40×), the infiltrates are more easily seen to be to be mononuclear cells surrounding areas of necrosis at 6 weeks (FIG. 14B). At 14 weeks, the inflammation extends into the surrounding parenchyma (FIG. 14C).

7.6. DETECTION AND QUANTITATION OF HBsAG IN RAT SERUM

To follow the course of infection, levels of HBsAg in rat serum were measured using an EIA kit for HBV surface antigen (Abbott Labs, Abbott Park, Ill.) according to the manufacturer's protocol. Briefly, 10 µl serum in 190 µl saline was mixed with anti-HBs (mouse) monoclonal antibody coated beads and 50 µl of horseradish peroxidase conjugated anti-mouse secondary antibody and incubated at room temperature for 16 hours. Then the incubation solution was removed and the beads were washed six times with 10 ml distilled water, and the beads were transferred to clean assay tubes and incubated with 300 µl of freshly prepared o-phenylenediamine substrate and quantitated using a spectrophotometer at 492 nm. Assays were done in triplicate and the results (see Tables 1, 2 and 3, third column) were expressed as means±S.D. in units of pg/ml serum.

7.8. DETECTION OF SERUM ALANINE AMINOTRANSFERASE (ALT)

To determine whether HBV infection was associated with any liver damage, serum was collected from rats as a function of time after injection, and serum ALT values determined in triplicate from 10 µl serum using a commercial ALT detection kit (Sigma). All assays were done in triplicate and results are expressed as means±S.D. International Units (IU)/ml.

Group 1 animals were treated by (i) intrafetal injections of human-hepatocytes into the peritoneums at 17 days post-conception; (ii) intrasplenic saline injection at birth; and (iii) one week later, purified HBV harvested from a human hepatoma cell line was administered by intrasplenic injection.

TABLE 1

| Time Post-HBV Injection (days) | ALT (IU/L) | HBsAg (pg/ml) |
| --- | --- | --- |
| 0 | 28 ± 15 | Not detectable |
| 1 | 44 ± 20 | Not detectable |
| 8 | 22 ± 12 | Not detectable |
| 10 | 25 ± 10 | Not detectable |

As shown in Table 1, animals that received no tolerization or human hepatocytes, but were injected with HBV had no significant changes in ALT as a measure of liver cell damage, or detectable HBsAg in the serum even as soon 1 day after injection of HBV through at least 10 days. The data confirm that HBV does not cause hepatic damage in rats and that the virus is rapidly cleared from the circulation.

Animals in Group 2 were treated by (i) intrafetal injection of human hepatocytes into the peritoneums at 17 days post-conception; (ii) intrasplenic injection of 2 million human primary hepatocytes at birth; and (iii) 1 week post hepatocyte transplantation, saline was injected intrasplenically.

TABLE 2

| Time Post-HBV Injection (days) | ALT (IU/L) | HBsAg (pg/ml) |
| --- | --- | --- |
| 0 | 25 ± 15 | Not detectable |
| 1 | 22 ± 20 | Not detectable |
| 8 | 30 ± 5 | Not detectable |
| 10 | 25 ± 16 | Not detectable |

As shown in Table 2, animals tolerized with human hepatocytes that received human hepatocyte transplants, but no HBV, also had normal ALT and undetectable HBsAg throughout the 10 days. Thus, without inoculation with HBV, there was no serological evidence of hepatotoxicity or circulating HBV.

Animals in Group 3 were treated by (i) intrauterine injection into the peritoneum at 17 days post-conception with human hepatocytes lysate; (ii) intrasplenic injection of 2 million human primary hepatocytes at birth; and (iii) HBV was injected intrasplenically at 1 week post-hepatocyte transplantation.

TABLE 3

| Time Post-HBV Injection (days) | ALT (IU/L) | HBsAg (pg/ml) |
|---|---|---|
| 0 | 22 ± 15 | Not detectable |
| 1 | 47 ± 0 | 0.2 ± .01 |
| 4 | 86 ± 15 | 0.1 ± .05 |
| 8 | 132 ± 15 | 0.4 ± 0.1 |
| 10 | 179 ± 20 | 0.5 ± .15 |

As shown in Table 3, in this group which was tolerized and received human hepatocytes and HBV, ALT levels were normal until day 4 when the level doubled to 86 IU/L. By day 10, the ALT had doubled again to 179 IU/L. The HBsAg was detectable at 0.1–0.2 pg/ml through day 4. However, the levels doubled to 0.4 and reached 0.5 pg/ml day 10. These data suggest that viral antigen and likely viral levels increase early in the process, and are followed by liver cell damage. This is supportive of an inflammatory process triggered by the injection of HBV, but only in animals that have human hepatocytes.

Various publications are cited herein, the contents of which are hereby incorporated by reference in their entireties.

What is claimed is:

1. A non-human mammal having a liver that comprises human hepatocytes, wherein the mammal has a normal immune system but (i) has been rendered tolerant to human hepatocytes by a method selected from the group consisting of intraperitoneal injection and intrathymic injection, of an effective amount of a composition selected from the group consisting of human hepatocytes and a human hepatocyte lysate, in a suitable carrier, during a time period selected from the group consisting of the period prior to birth of the mammal and the period after birth when the mammal is a neonate, and (ii) has subsequently received a transplant comprising human hepatocytes.

2. The non-human mammal of claim 1, where the mammal is a mouse which carries a transgene which is a urokinase gene operably linked to an albumin promoter.

3. A method of preparing a non-human mammal having a liver comprising human hepatocytes, comprising the steps of:
   (i) inducing tolerance in a non-human host mammal toward hepatocytes from a human donor by a method selected from the group consisting of intraperitoneally injecting and intrathymically injecting an effective amount of a composition selected from the group consisting of human hepatocytes and a human hepatocyte lysate, in a suitable carrier, during a time period selected from the group consisting of the period prior to birth of the mammal and the period after birth when the mammal is a neonate, and
   (ii) introducing hepatocytes from the human donor into the tolerized mammal produced in step (i) where the number of hepatocytes introduced are effective in colonizing the liver of the non-human mammal.

4. The method of claim 3 where the mammal is a mouse which carries a hepatotoxic transgene which is a urokinase gene operably linked to an albumin promoter.

5. The method of claim 3 where tolerance is induced by intraperitoneal injection of said composition.

6. The method of claim 3 where tolerance is induced by intrathymic injection of said composition.

7. A method for identifying a toxic effect of a test agent, comprising the steps of:

(a) administering the test agent to a non-human mammal having a liver that comprises human hepatocytes, wherein the mammal has a normal immune system but (i) has been rendered tolerant to human hepatocytes by a method selected from the group consisting of intraperitoneal injection and intrathymic injection, of an effective amount of a composition selected from the group consisting of human hepatocytes and a human hepatocyte lysate, in a suitable carrier, during a time period selected from the group consisting of the period prior to birth of the mammal and the period after birth when the mammal is a neonate, and (ii) has received a transplant comprising human hepatocytes; and (b) subsequently evaluating whether changes have occurred in the viability of human hepatocytes in the mammal.

8. A model system for alcohol-associated liver disease comprising a non-human mammal having a liver that comprises human hepatocytes, wherein the mammal has a normal immune system but (i) has been rendered tolerant to human hepatocytes by a method selected from the group consisting of intraperitoneal injection and intrathymic injection, of an effective amount of a composition selected from the group consisting of human hepatocytes and a human hepatocyte lysate, in a suitable carrier, during a time period selected from the group consisting of the period prior to birth of the mammal and the period after birth when the mammal is a neonate, and (ii) has received a transplant comprising human hepatocytes, where the non-human mammal has been administered an amount of alcohol effective in producing hepatocellular degenerative changes.

9. A model system for a liver disease caused by Hepatitis B virus, comprising a non-human mammal having a liver that comprises human hepatocytes infected by Hepatitis B virus, wherein the mammal has a normal immune system but (i) has been rendered tolerant to human hepatocytes by a method selected from the group consisting of intraperitoneal injection and intrathymic injection, of an effective amount of a composition selected from the group consisting of human hepatocytes and a human hepatocyte lysate, in a suitable carrier, during a time period selected from the group consisting of the period prior to birth of the mammal and the period after birth when the mammal is a neonate, and (ii) has received a transplant comprising human hepatocytes, wherein Hepatitis B virus infection of the hepatocytes occurs before or after transplantation.

* * * * *